(12) United States Patent
Ranch et al.

(10) Patent No.: US 7,022,894 B2
(45) Date of Patent: Apr. 4, 2006

(54) METHODS OF TRANSFORMING PLANTS AND IDENTIFYING PARENTAL ORIGIN OF A CHROMOSOME IN THOSE PLANTS

(75) Inventors: Jerome P. Ranch, West Des Moines, IA (US); Wallace A. Marsh, Ankeny, IA (US); Dwight T. Tomes, Van Meter, IA (US); Zuo-Yu Zhao, Johnston, IA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 0 days.

(21) Appl. No.: 10/784,418

(22) Filed: Feb. 23, 2004

(65) Prior Publication Data

US 2004/0194161 A1    Sep. 30, 2004

Related U.S. Application Data

(63) Continuation of application No. 09/907,411, filed on Jul. 17, 2001, now abandoned.

(60) Provisional application No. 60/218,895, filed on Jul. 18, 2000.

(51) Int. Cl.
*A01H 1/00* (2006.01)
*A01H 1/02* (2006.01)
*A01H 5/00* (2006.01)

(52) U.S. Cl. .................... 800/268; 800/275; 800/320.1

(58) Field of Classification Search ................ 800/260, 800/268, 269, 275, 320.1; 435/410, 412, 435/424, 430, 430.1, 468, 469, 470
See application file for complete search history.

(56) References Cited

U.S. PATENT DOCUMENTS

| | | | |
|---|---|---|---|
| 5,492,547 A | 2/1996 | Johnson | |
| 5,689,053 A | 11/1997 | Robert et al. | |
| 5,850,009 A * | 12/1998 | Kevern | 800/271 |
| 5,981,584 A | 11/1999 | Egbertson et al. | |
| 5,981,832 A | 11/1999 | Johnson | |
| 5,981,840 A * | 11/1999 | Zhao et al. | 800/294 |
| 5,989,915 A | 11/1999 | Christou et al. | |
| 6,368,300 B1 | 4/2002 | Freestone et al. | |
| 6,512,167 B1 | 1/2003 | Carolo | |

FOREIGN PATENT DOCUMENTS

| | | |
|---|---|---|
| WO | WO 91/10725 A1 | 7/1991 |
| WO | WO 9905903 A1 | 2/1999 |
| WO | WO 99/28521 A1 | 5/1999 |

OTHER PUBLICATIONS

Paterson et al., Regeneration of Helianthus Annus Inbred Plants from Callus, Plant Science (1995) 42:125-132.
Teutonico et al., Mapping of RFLP and qualitative trait looi in Brassica rapa and comparison to the linkage maps of B. napus, B. aleracea, and Arabidopsis thallana, Theor Appl Genet (1994) 89:885-894.
Knittel et al., Transformation of sunflower (*Helianthus annua L*): a reliable protocol. Cell Reports (1994) 14:81-88.
Staub et al., Genetic Markers, Map Construction, and Their Application in Plant Breeding, HortScience (1996) 31(5): 729-738.
Choi et al., High frequency of cytogenetic aberration in transgenic oat (*Avena sativa L.*) plants, Plant Science (2000) 158:85-94.

* cited by examiner

*Primary Examiner*—David H. Kruse
*Assistant Examiner*—Keith O. Robinson
(74) *Attorney, Agent, or Firm*—Pioneer Hi-Bred International, Inc.

(57) ABSTRACT

Methods for plant transformation, for improving transformation efficiency, and for producing transgenic plants are provided. The methods comprise crossing a recipient plant from a genetic line of a plant species of interest with a donor plant selected from a transformation competent genetic line of the same plant species or of another closely related plant species to obtain a hybrid plant. Tissues obtained from the hybrid plant are transformation competent. These tissues can then be transformed with one or more nucleotide sequences of interest and selected for transgenic events having the nucleotide sequence of interest integrated within a chromosome derived from the recipient plant. Transformed cells can be selected and transgenic hybrid plants regenerated. The nucleotide sequence of interest can be introgressed into the genetic line from which the original recipient parent was derived, or into other genetic lines. Transformed plants and seeds are additionally provided.

3 Claims, 7 Drawing Sheets

Figure 1:
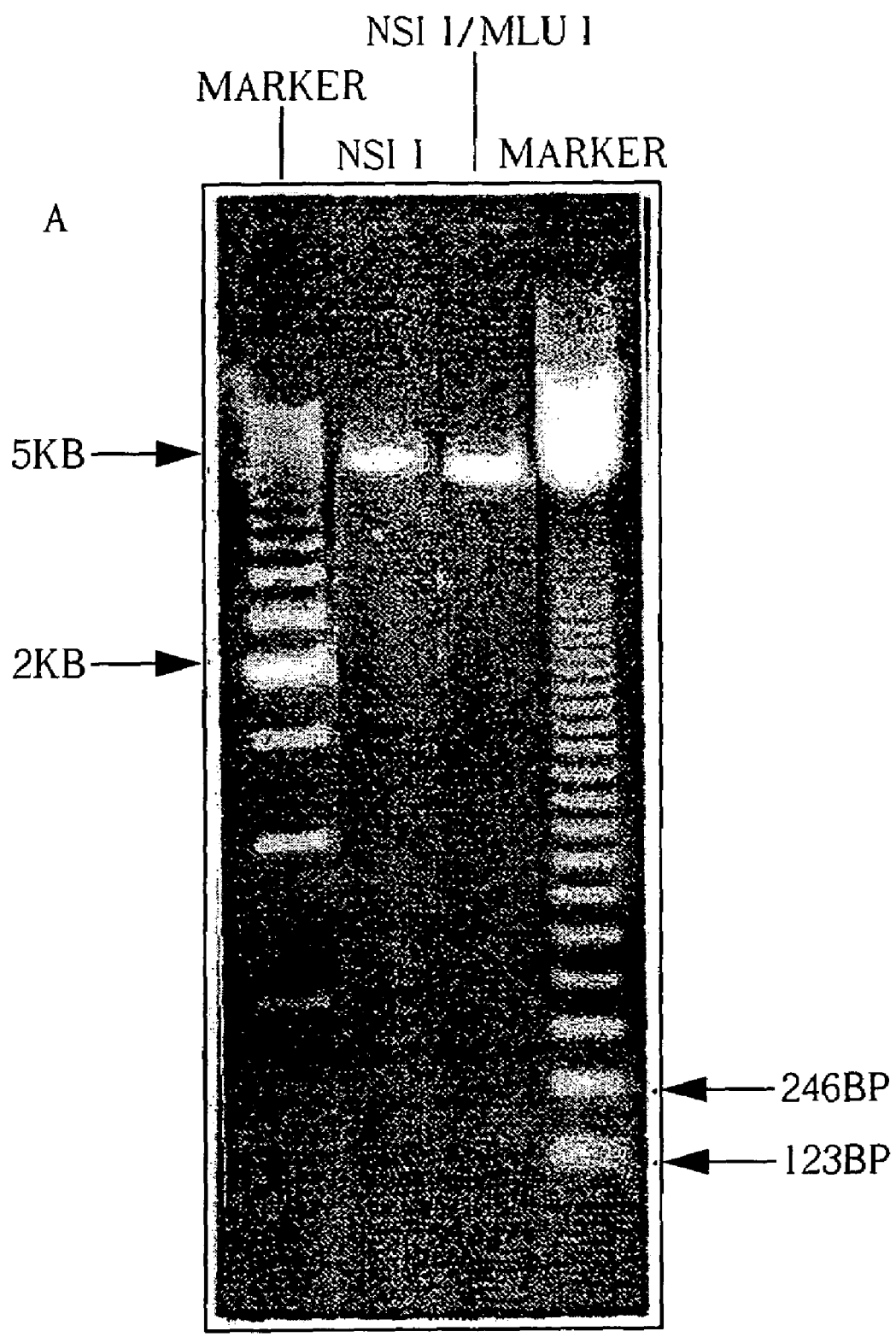
Figure 2:
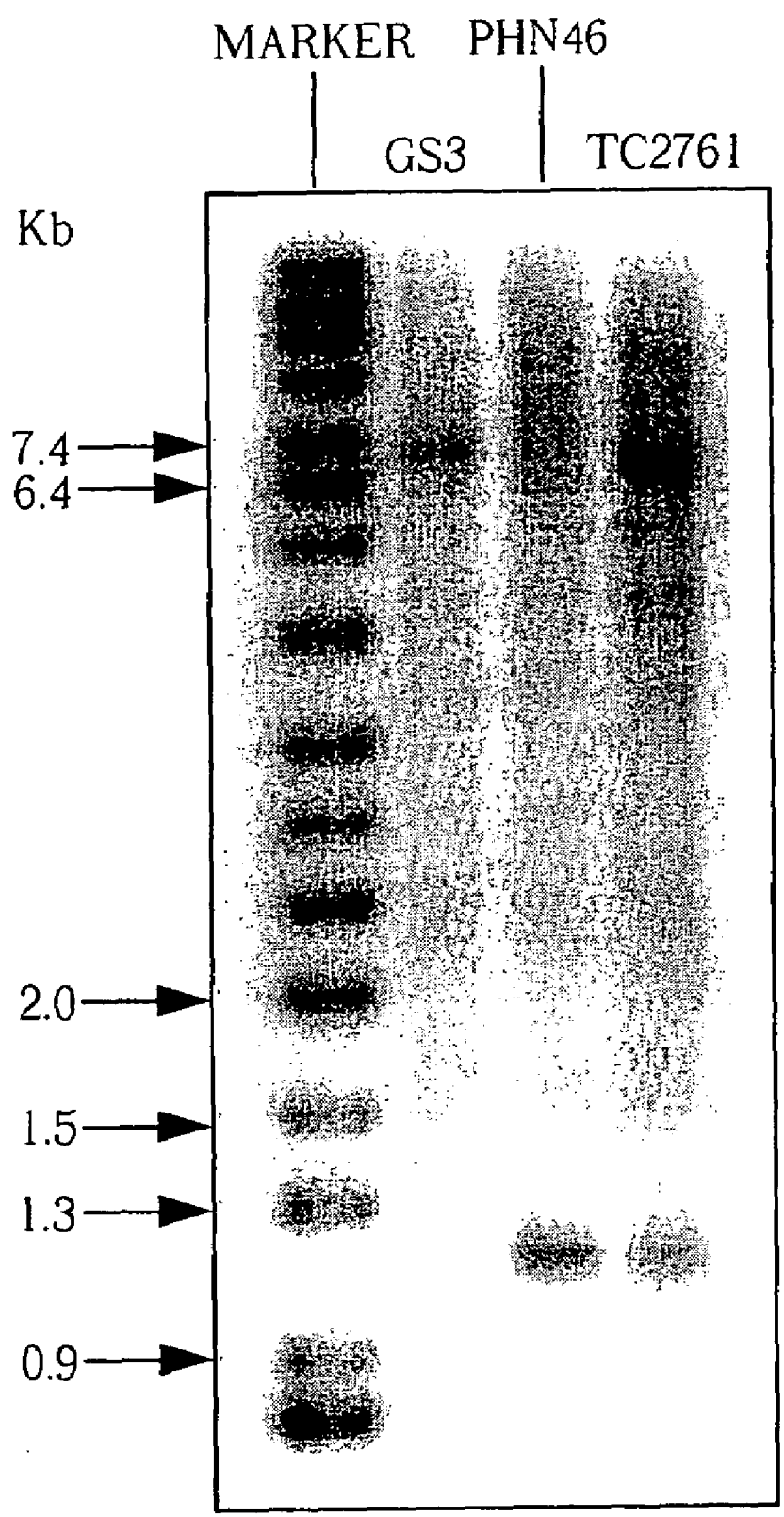
Figure 4A:
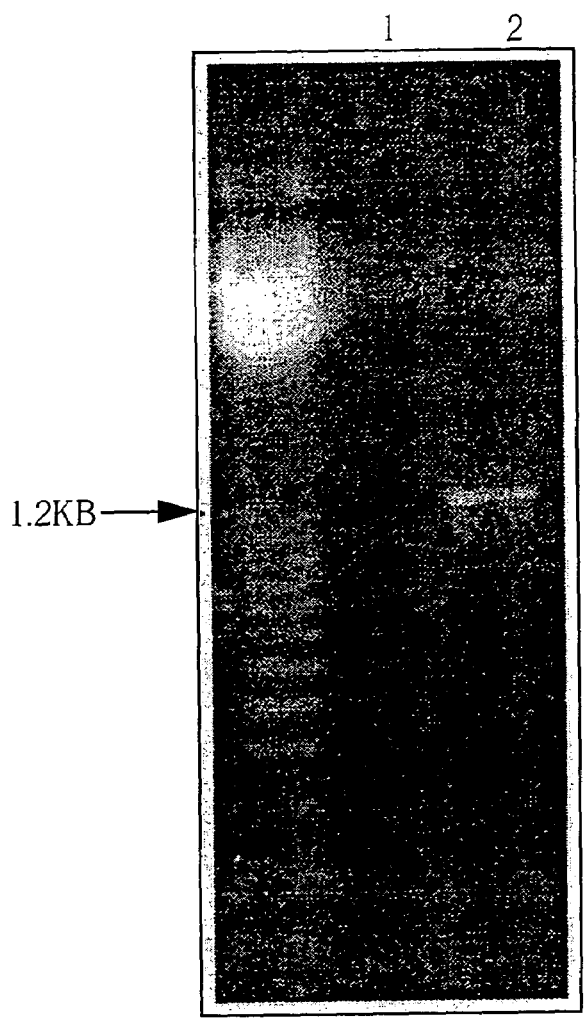
Figure 4B:
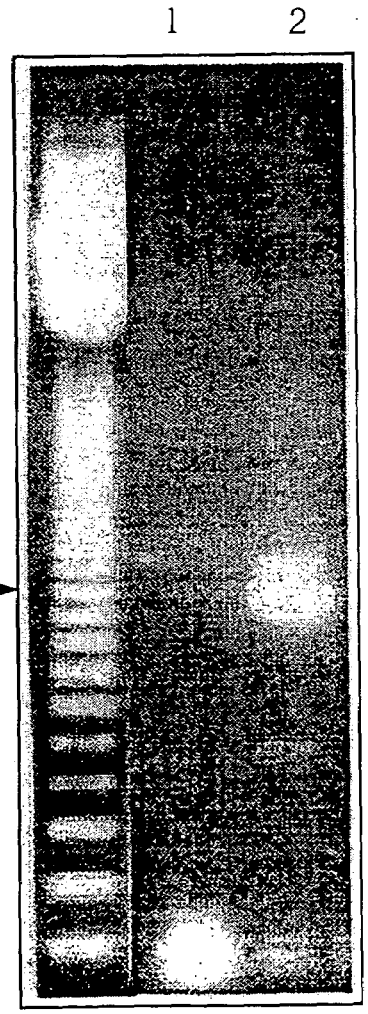
Figure 5:
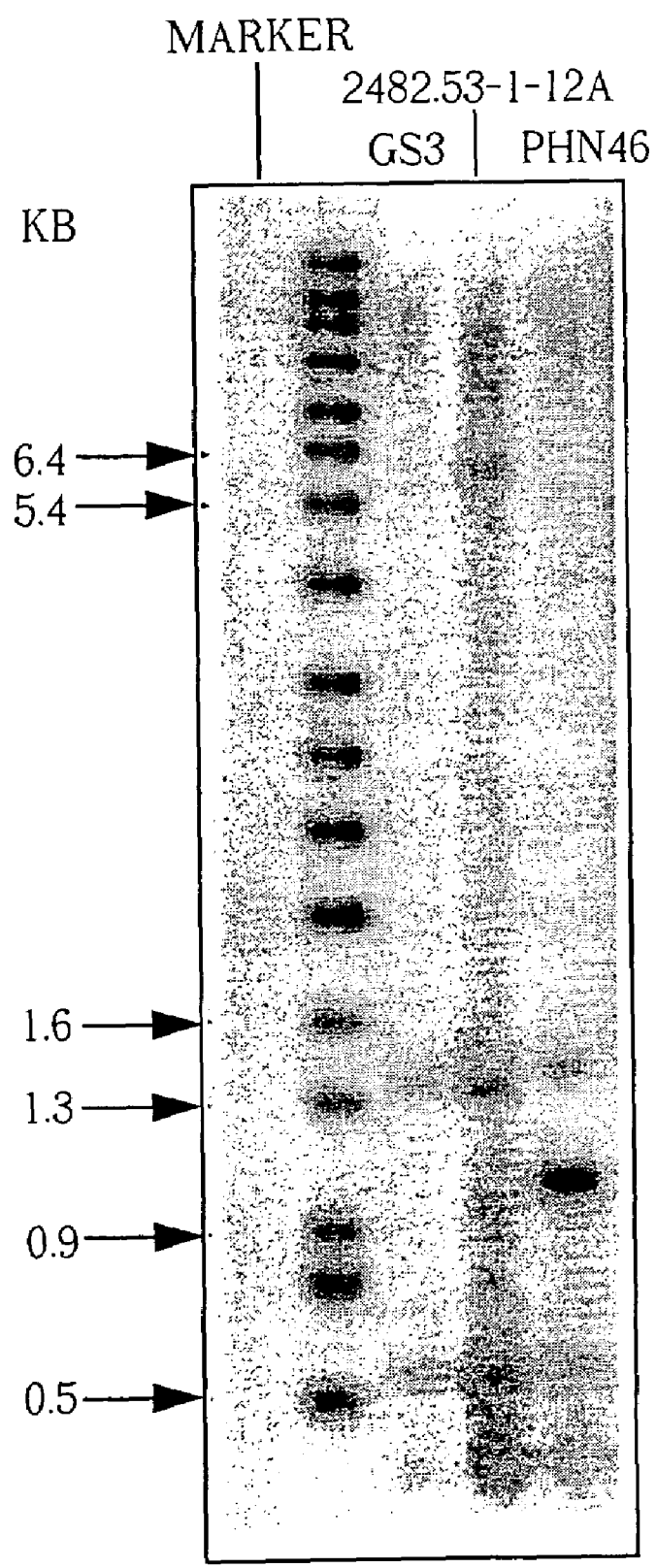

| | |
|---|---|
| CLONE 28 | GGTTTTGTAG ATTTTAATTT TGGAAAACAG AGAACACGGC TGAACTTTAC |
| GS3 | GGTTTTGTAG ATTTTAATTT TGGAAAACAG AGAACACGGC TGAACTTTAC |
| PHN46 | GGTTTTGTAG ATTTGAGTTT TGGAAAACAG AGAACACAGC TGAACTTTAC |
| TC2740 | GGTTTTGTAG ATTTTAATTT TGGAAAACAG AGAACACGGC TGAACTTTAC |

GGTTTTGTAG ATTTTAATTT TGGAAAACAG AGAACACGGC TGAACTTTAC

| | |
|---|---|
| CLONE 28 | AAAGGGCTAA AAATTCAGTT CTGAATTTTC TGAATTTCCT TTTTGAAGTT |
| GS3 | AAAGGGCTAA AAATTCAGTT CTGAATTTTC TGAATTTCCT TTTTG |
| PHN46 | AAAGGGCTAA AAATTCAGTT CTGAATTTTC TGAATTTCCC TTTTGAAGTT |
| TC2740 | AAAGGGCTAA AAATTCAGTT CTGAATTTTC TGAATTTCCT TTTTGAAGTT |

AAAGGGCTAA AAATTCAGTT CTGAATTTTC TGAATTTCCT TTTTGAAGTT

| | |
|---|---|
| CLONE 28 | TAGCTTCAAG GGTCTTTTTG AGAATTTTGC AAAGCTTTGC TGATCAAACT |
| PHN46 | TAGCTTCAAC GGTCCTT |
| TC2740 | TAGCTTCAAG GGTCTTTTTG AGAATTTTGC AAAGCTTTGC TGATCAAACT |

TAGCTTCAAG GGTCTTTTTG AGAATTTTGC AAAGCTTTGC TGATCAAACT

Fig. 3

| | |
|---|---|
| JR451 | TCGCGTCACA TTCAGAGTTA TGGTTACTTG CTGCTGTGTC TACTGCTGTT |
| GS3 | ATTACTCG CTGCCGTGTC TACTGCTGTT |
| 2482.53-1-12B | TTACTTG CTGCTGTGTC TACTGCTGTT |
| PHN46 | TTACTTG CTGCTGTGTC TACTGCTGTT |

TCGCGTCACA TTCAGAGTTA TGRTTACTTG CTGCTGTGTC TACTGCTGTT
. . .

| | |
|---|---|
| JR451 | GCTTTTCCAT TGCCATGCTT TGCTGCCGAT GACGAGGATG ATGTTGAGCT |
| GS3 | GCTTTTCCAT TGCCATGCTT TGCTGCCGAC GACAAGGATG ATGTTGAGCT |
| 2482.53-1-12B | GCTTTTCCAT TGCCATGCTT TGCTGCCGAT GACGAGGATG ATGTTGAGCT |
| PHN46 | GCTTTTCCAT TGCCATGCTT TGCTGCCGAT GACGAGGATG ATGTTGAGCT |

GCTTTTCCAT TGCCATGCTT TGCTGCCGAT GACGAGGATG ATGTTGAGCT
. .

| | |
|---|---|
| JR451 | CCACCATGTT GGCTCGCTTG AAGACCACCG CTGCCCGTGG TATGCTGCCA |
| GS3 | CCACCATGTT GGCTCGCTTG TAGACCACCG CTGCCCGTGG TATGCTGCCA |
| 2482.53-1-12B | CCACCATGTT GGCTCGCTTG AAGACCACCG CTGCCCGTGG TATGCTGCCA |
| PHN46 | CCACCATGTT GGCTCGCTTG AAGACCACCG CTGCCCGTGG TATGCTGCCA |

CCACCATGTT GGCTCGCTTG AAGACCACCG CTGCCCGTGG TATGCTGCCA
. .

| | |
|---|---|
| JR451 | TGCCTCCTCT TCCAAGTGGT GGTAATACGC CACCGCTGCT CTGCTCTAAT |
| GS3 | TGCCTCCTCT TCCAAGTGGT GGGAATACGC CACAGCTACT CT::::: AAT |
| 2482.53-1-12B | TGCCTCCTCT TCCAAGTGGT GGTAATACGC CACCGCTGCT CTGCTCTAAT |
| PHN46 | TGCCTCCTCT TCCAAGTGGT GGTAATACGC CACCGCTGCT CTGCTCTAAT |

TGCCTCCTCT TCCAAGTGGT GGTAATACGC CACCGCTGCT CTGCTCTAAT
. . .....

| | |
|---|---|
| JR451 | GGGCGAGGTG GGCGCTGGTT CGTCTGCTAC TAGGGTTGGC TGTTTTGGTG |
| GS3 | GGGCAAGGCG GGCGCTGGTT TGTCTGCTGC TAGGGTTGGC TGTTTTGGTG |
| 2482.53-1-12B | GGGCGAGGTG GGCGCTGGTT CGTCTGCTAC TAGGGTTGGC TGTTTTGGTG |
| PHN46 | GGGCGAGGTG GGCGCTGGTT CGTCTGCTAC TAGGGTTGGC TGTTTTGGTG |

GGGCGAGGTG GGCGCTGGTT CGTCTGCTAC TAGGGTTGGC TGTTTTGGTG
. . . . . .

| | |
|---|---|
| JR451 | GGCTA |
| GS3 | GGTTGGGCCA TGAGAATTAT GCACTGGGCC AATAGAAGAG CTCTTCAC |
| 2482.53-1-12B | GGCTAGGCCG TGAGAATTAT GAACTGGGCA GATAGAAGAG CTCTTCAC |
| PHN46 | GGCTAGGCCG TGAGAATTAT GAACTGGGCA GATAGAAGAG CTCTTCAC |

GGCTAGGCCG TGAGAATTAT GAACTGGGCA GATAGAAGAG CTCTTCAC
.. . .. .

Fig. 6

METHODS OF TRANSFORMING PLANTS AND IDENTIFYING PARENTAL ORIGIN OF A CHROMOSOME IN THOSE PLANTS

CROSS-REFERENCE TO RELATED APPLICATIONS

This application claims priority to U.S. patent application Ser. No. 09/907,411 filed Jul. 17, 2001 as a continuation, now abandoned which claims benefit of U.S. Provisional Application Ser. No. 60/218,895 filed Jul. 18, 2000, the disclosures of which are incorporated herein by reference.

FIELD OF THE INVENTION

The present invention relates to the field of genetic engineering of plants and to methods for introducing traits into plants.

SUMMARY OF THE INVENTION

Methods for plant transformation, for improving transformation efficiency, and for producing desired transgenic plants are provided.

DETAILED DESCRIPTION OF THE INVENTION

Methods for improving transformation and transformation efficiency in a plant are provided, especially with regard to introgression of a transferred DNA into a chosen inbred. The methods comprise sexually crossing a recipient parent plant chosen from a genetic line of a plant species of interest with a donor parent plant selected from a more transformation-competent genetic line of the plant species, or of another closely related plant species, to obtain an F1 hybrid progeny. An F1 hybrid can also be obtained through non-sexual means and is not limited to in-vivo techniques. A cell obtained from the F1 hybrid progeny can then be transformed with one or more nucleotide sequences of interest. The donor parent plant typically is highly transformable but could be of limited, or perhaps deleterious, breeding value. The recipient parent plant typically is a recalcitrant inbred used in product development that exhibits no or poor transformability. When the F1 hybrid between recipient plant and donor plant is made, the disparate phenotypes of the parents are reconciled to produce cells and a plant with a hybrid phenotype consisting of higher transformability than the recipient parent. In addition, the F1 hybrid phenotype offers the potential to introduce a transgene into a chromosome derived from the recipient plant. The DNA flanking the transgene can be used to identify the parental origin of the chromosome containing the transgene, and transgenic events identified as containing transgenes in the chromosome from the recipient parent plant are regenerated.

By "improving transformation efficiency" is intended that the number of transformed plants recovered per unit time and per unit resource is increased at least about two-fold, at least about five-fold, or at least about ten-fold. It is recognized that in some instances, particularly in inbred plants, particularly those inbreds exhibiting little or no transformation capability, transformation is made possible by the methods of the present invention. The methods of the invention provide a more efficient means for introducing foreign DNA into plants, particularly inbred lines of plants, more particularly those plant genetic lines that are recalcitrant to transformation. The invention allows for the direct insertion of the foreign DNA into a chromosome derived from the recipient plant with high frequency, thus reducing the number of backcrosses to obtain a transgenic plant having desired characteristics of the genetic line from which the recipient parent plant is derived. Thus, the invention improves the production efficiency of transformants as well as reduces backcrossing time to introgress a transgene into a transgenic plant of interest, particularly an inbred, having the nucleotide sequence of interest incorporated in its genome.

By "transformation" is intended the genetic manipulation of the plant, cell, cell line, callus, tissue, plant part, seed, and the like. That is, such cell, cell line, callus, tissue, plant part, seed, or plant has been altered by the presence of recombinant DNA wherein said DNA is introduced into the genetic material within the cell. Preferably, the DNA is introduced into a chromosome. Recombinant DNA includes foreign DNA, heterologous DNA, exogenous DNA, chimeric DNA, and endogenous DNA wherein said endogenous DNA has been derived from the natural chromosomal site within the plant.

By "recipient parent" is intended a plant selected from a genetic line of a plant species of interest. Generally, the recipient parent will be a genotype that is recalcitrant to transformation, generally an inbred plant, and more particularly a recalcitrant inbred plant that possesses high breeding value and is used in development and production of products. By "recalcitrant" is intended the genotype of plant exhibits a low level of transformation efficiency relative to the donor parent, and few or no transgenic events per unit time and resource can be produced. Thus a recipient parent that is recalcitrant to transformation, in the current art has a transformation efficiency that is less than GS3.

By "donor parent" is intended a plant selected from a genetic line of a plant species of interest that is transformation competent, but may be of limited agronomic value. That is, a useful level of transformation efficiency is observed in the plant, plant cell or plant part thereby effecting a greater throughput of transgenic events. Generally, a useful level of transformation efficiency comprises an efficiency of at least about 5% (720 transgenic events/year/person), often greater than 30% (4300 transgenic events/year/person), more often greater than 20% (2900 transgenic events/year/person), and most often greater than 10% (1400 transgenic events/year/person). Thus, by "transformation competent" is intended a level of transformation efficiency of at least about 5%. In maize, for example, donor parents include but are not limited to Hi-II, A188, H99, DAB01, DAB02, DAB012, and other lines that generate type II callus when cultured, and/or that exhibit high transformation efficiency. The donor parent may be from the same plant species as the recipient parent, or may be from another closely related plant species. By "closely related plant species" is intended the two species are sexually compatible, that is, they form viable seed following cross-pollination, and are capable of producing fertile hybrid progeny.

By "F1 hybrid" is intended a plant or plant cell resulting from a cross between a recipient parent of the invention and a donor parent of the invention. This cross can occur naturally by, for example, sexual reproduction, or artificially by, for example in vitro nuclear fusion. The F1 hybrid plants of the invention will contain approximately one half of the genetic complement of the donor parent, i.e., that chromosomal material whose ancestral origin resides with the donor parent, and approximately one half of the genetic complement of the recipient parent, i.e., that chromosomal material whose ancestral origin resides with the recipient parent. For purposes of the present invention, a chromosome having an ancestral origin residing with a donor parent is referred to as a "donor chromosome", while a chromosome having an ancestral origin residing with the recipient parent is referred to as a "recipient chromosome". Similarly, when reference is made to a chromosome "derived" from a donor parent or a recipient parent, it is intended that the chromosome has an ancestral origin residing with a donor parent or with a recipient parent, respectively. While the donor parent may be used as either the male parent or female parent in the cross, it may be preferable to use the donor parent as the female parent, as a higher transformation efficiency is observed with this type of cross in some cases.

By "flanking DNA" is intended DNA genetically and/or physically linked to the site of integration of a transferred DNA. Such flanking DNA can range in size from a single base pair to an entire linear or circular DNA molecule.

By "amplified" is meant the construction of multiple copies of a nucleic acid sequence or multiple copies complementary to the nucleic acid sequence using at least one of the nucleic acid sequences as a template. Amplification systems include the polymerase chain reaction (PCR) system, ligase chain reaction (LCR) system, nucleic acid sequence based amplification (NASBA, Cangene, Mississauga, Ontario), Q-Beta Replicase systems, transcription-based amplification system (TAS), and strand displacement amplification (SDA). See, e.g., Diagnostic Molecular Microbiology: Principles and Applications, D. H. Persing et al., Ed., American Society for Microbiology, Washington, D.C. (1993). The product of amplification is termed an amplicon.

By "adapters" is intended small, linear segments of double-stranded DNA. Such adapters and methods of their synthesis and use are known to those of ordinary skill in the art. Generally, such adapters are 5–50 base pairs in length and are prepared by synthesizing two separate single-stranded DNA molecules that are at least partially complementary and placing the two molecules together in conditions that favor the formation of double-stranded DNA. A "bubble adapter" is a type of adapter that comprises two single-stranded DNA molecules that when annealed has at least one internal region that is not complementary.

As used herein, "nucleic acid" includes reference to a deoxyribonucleotide or ribonucleotide polymer, or chimeras thereof, in either single- or double-stranded form, and unless otherwise limited, encompasses known analogues having the nature of natural nucleotides in that they hybridize to single-stranded nucleic acids in a manner similar to naturally occurring nucleotides (e.g., peptide nucleic acids).

By "transferred DNA" is intended at least one nucleotide sequence that may function to change the phenotype of the plant, such as a coding sequence for a gene of interest. Particular genes of interest include those that provide a readily analyzable functional feature to the host cell and/or organism, such as marker genes, transgenes as well as other genes that alter the phenotype of the recipient cells, and the like. Thus, genes affecting plant growth, height, susceptibility to disease, insects, nutritional value, oil quality, starch content, glucan content, amino acid content and the like may be utilized in the invention. The nucleotide sequence may be a sequence for a gene fragment that can be targeted for replacement of a fragment of a naturally occurring gene of interest using gene-targeting methods known in the art. The nucleotide sequence also may encode an "antisense" sequence to turn off or modify gene expression. It can include transgenes, transposable elements and polynucleotides of all lengths and purpose, coding and non-coding.

As used herein, the term "plant" includes reference to whole plants, plant organs (e.g., leaves, stems, roots, etc.), seeds and plant cells and progeny of same. "Plant cell", as used herein includes, without limitation, seeds, suspension cultures, embryos, meristematic regions, callus tissue, leaves, roots, shoots, gametophytes, sporophytes, pollen, and microspores. The class of plants which can be used in the methods of the invention include both monocotyledonous and dicotyledonous plants.

As used herein, "transgenic plant" includes reference to a plant which comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic plant material. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

Recipient genotypes that may function in hybrid combination with Hi-II, A188 or another donor parent for transformation include PHTE4, PHAA0, PHP18, PH05F, PH09B, PHP02, PHJ90, PH24E, PHN46, PHT05, ASKC27 PH21T, PHR8K, PHH3V, PHW0Y, PHG9B, PHK9D, PHT7G, PHJ9D, PHE8D, PHZ3V, PHZ6C, PHV2E, PHN8Y, PHBE2, PH08A, PH14T, PH224, PH5WB, Gaspe Flint or one of the following U.S. Pat. Nos.

| | | |
|---|---|---|
| 6,025,547 | Feb. 15, 2000 | Inbred maize line PH1CA; |
| 6,020,543 | Feb. 1, 2000 | Inbred maize line PH1B5; |
| 5,998,711 | 07-Dec-99 | Inbred Maize Line PH09E |
| 5,990,393 | 23-Nov-99 | Inbred Maize Line PH1CN; |
| 5,986,185 | 16-Nov-99 | Inbred Maize Line PH24D; |
| 5,986,184 | 16-Nov-99 | Inbred Maize Line PH1TB; |
| 5,977,456 | 02-Nov-99 | Inbred Maize Line PH1M7; |
| 5,977,451 | 02-Nov-99 | Inbred Maize Line PHFW4; |
| 5,948,957 | 07-Sep-99 | Inbred Maize Line PH19V; |
| 5,942,671 | 24-Aug-99 | Inbred Maize Line PH185; |
| 5,942,670 | 24-Aug-99 | Inbred Maize Line PH14T; |
| 5,939,608 | 17-Aug-99 | Inbred Maize Line PH08O; |
| 5,939,607 | 17-Aug-99 | Inbred Maize Line PH2CB; |
| 5,936,148 | 10-Aug-99 | Inbred Maize Line PH1GC; |
| 5,929,313 | 27-Jul-99 | Inbred Maize Line PHMJ2; |
| 5,917,134 | 29-Jun-99 | Inbred Maize Line PHDN7; |
| 5,917,125 | 29-Jun-99 | Inbred Maize Line PHO3D; |
| 5,889,188 | 30-Mar-99 | Inbred Maize Line PH0B4; |
| 5,866,768 | 02-Feb-99 | Inbred Maize Line PH02T; |
| 5,866,767 | 02-Feb-99 | Inbred Maize Line PH79A; |
| 5,859,354 | 12-Jan-99 | Inbred Maize Line PH09B; |
| 5,859,316 | 12-Jan-99 | Inbred Maize Line PH0HR; |
| 5,859,313 | 01-Jan-99 | Inbred Maize Line PHKV0; |
| 5,850,010 | 15-Dec-98 | Inbred Maize Line PH56C; |
| 5,850,009 | 15-Dec-98 | Inbred Maize Line PH0HC; |
| 5,850,007 | 15-Dec-98 | Inbred Maize Line PH1MR; |
| 5,844,117 | 01-Dec-98 | Inbred Maize Line PH0GP; |
| 5,844,116 | 01-Dec-98 | Inbred Maize Line PH1W2; |
| 5,841,015 | 24-Nov-98 | Inbred Maize Line PH05G; |
| 5,824,847 | 20-Oct-98 | Inbred Maize Line PH22G; |
| 5,824,845 | 20-Oct-98 | Inbred Maize Line PH10A; |
| 5,811,637 | 22-Sep-98 | Inbred Maize Line PH40B; |
| 5,792,915 | 11-Aug-98 | Inbred Maize Line PH0AV; |
| 5,792,912 | 11-Aug-98 | Inbred Maize Line PH00M; |

-continued

| | | |
|---|---|---|
| 5,792,911 | 11-Aug-98 | Inbred Maize Line PH24M; |
| 5,770,790 | 23-Jun-98 | Inbred Maize Line PH41E; |
| 5,767,340 | 16-Jun-98 | Inbred Maize Line PHBR2; |
| 5,763,757 | 09-Jun-98 | Inbred Maize Line PH07D; |
| 5,763,746 | 09-Jun-98 | Inbred Maize Line PH20A; |
| 5,763,744 | 09-Jun-98 | Inbred Maize Line PH67A; |
| 5,763,743 | 09-Jun-98 | Inbred Maize Line PH63A; |
| 5,750,849 | 12-May-98 | Inbred Maize Line PH05W; |
| 5,750,847 | 12-May-98 | Inbred Maize Line PH38D; |
| 5,750,835 | 12-May-98 | Inbred Maize Line PH47A; |
| 5,750,834 | 12-May-98 | Inbred Maize Line PH80B; |
| 5,750,832 | 12-May-98 | Inbred Maize Line PH44G; |
| 5,750,831 | 12-May-98 | Inbred Maize Line PH25A; |
| 5,750,830 | 12-May-98 | Inbred Maize Line PH15A; |
| 5,750,829 | 12-May-98 | Inbred Maize Line PH0AA; |
| 5,731,493 | 24-Mar-98 | Inbred Maize Line PH63B; |
| 5,731,492 | 24-Mar-98 | Inbred Maize Line PH19A; |
| 5,731,491 | 24-Mar-98 | Inbred Maize Line PHNG2; |
| 5,728,919 | 17-Mar-98 | Inbred Maize Line PHBF0; |
| 5,723,723 | 03-Mar-98 | Inbred Maize Line PH44A; |
| 5,723,722 | 03-Mar-98 | Inbred Maize Line PHND1; |
| 5,708,189 | 13-Jan-98 | Inbred Corn Line PHP38; |
| 5,675,066 | 17-Oct-97 | Inbred Maize Line PH06N; |
| 5,639,946 | 17-Jun-97 | Inbred Maize Line PHDP0; |
| 5,633,427 | 27-May-97 | Inbred Corn Line PPHHB4; |
| 5,625,133 | 29-Apr-97 | Inbred Maize Line PH0C7; |
| 5,625,132 | 29-Apr-97 | Inbred Maize Line PH08B; |
| 5,625,129 | 29-Apr-97 | Inbred Corn Line PHDD6; |
| 5,618,987 | 08-Apr-97 | Inbred Maize Line PH42B; |
| 5,608,140 | 04-Mar-97 | Inbred Maize Line PH38B; |
| 5,608,139 | 04-Mar-97 | Inbred Maize Line PH05F; |
| 5,608,138 | 04-Mar-97 | Inbred Maize Line PHKV1; |
| 5,602,318 | 11-Feb-97 | Inbred Maize Line PHDG1; |
| 5,602,317 | 11-Feb-97 | Inbred Maize Line PHAA0; |
| 5,569,822 | 29-Oct-96 | Inbred Maize Line PHTE4; |
| 5,569,821 | 29-Oct-96 | Inbred Corn Line PHT11; |
| 5,569,819 | 29-Oct-96 | Inbred Maize Line PHPP8; |
| 5,569,818 | 29-Oct-96 | Inbred Maize Line PHAP8; |
| 5,569,817 | 29-Oct-96 | Inbred Maize Line PHJJ3; |
| 5,569,816 | 29-Oct-96 | Inbred Maize Line PHAJ0; |
| 5,567,861 | 22-Oct-96 | Inbred Corn Line PHN46; |
| 5,563,325 | 08-Oct-96 | Inbred Maize Line PHBE2; |
| 5,563,322 | 08-Oct-96 | Inbred Maize Line PHAG6; |
| 5,563,321 | 08-Oct-96 | Inbred Maize Line PHGF5; |
| 5,563,320 | 08-Oct-96 | Inbred Maize Line PH54B; |
| 5,557,038 | 17-Sep-96 | Inbred Maize Line PHTP9; |
| 5,557,034 | 17-Sep-96 | Inbred Corn Line PHN18; |
| 5,545,814 | 13-Aug-96 | Inbred Maize Line PHFR8; |
| 5,545,813 | 13-Aug-96 | Inbred Maize Line PHRF5; |
| 5,545,812 | 13-Aug-96 | Inbred Maize Line PHNJ2; |
| 5,545,809 | 13-Aug-96 | Inbred Maize Line PHBG4; |
| 5,543,575 | 06-Aug-96 | Inbred Corn Line PHK46; |
| 5,541,352 | 30-Jul-96 | Inbred Corn Line PHRD6; |
| 5,534,661 | 09-Jul-96 | Inbred Maize Line PHKW3; |
| 5,530,184 | 25-Jun-96 | Inbred Maize Line PHAP1; |
| 5,527,986 | 18-Jun-96 | Inbred Corn Line PHTD5; |
| 5,506,368 | 09-Apr-96 | Inbred Corn Line PHN82; |
| 5,506,367 | 09-Apr-96 | Inbred Corn Line PHP38; |
| 5,495,069 | 27-Feb-96 | Inbred Corn Line PHTE4; |
| 5,495,065 | 27-Feb-96 | Inbred Corn Line PHW06; |
| 5,491,286 | 13-Feb-96 | Inbred Corn Line PHKM5; |
| 5,476,999 | 19-Dec-95 | Inbred Corn Line PHR63; |
| 5,463,173 | 31-Oct-95 | Inbred Corn Line PHR61; |
| 5,453,564 | 26-Sep-95 | Inbred Corn Line PHTE4; |
| 5,444,178 | 22-Aug-95 | Inbred Corn Line PHHB4; |
| 5,436,390 | 25-Jul-95 | Inbred Corn Line PHR03; |
| 5,434,346 | 18-Jul-95 | Inbred Corn Line PHT11; |
| 5,416,254 | 16-May-95 | Inbred Corn Line PHRE1; |
| 5,387,755 | 07-Feb-95 | Inbred Corn Line PHFA5; |
| 5,387,754 | 07-Feb-95 | Inbred Corn Line PHGW7; |
| 5,367,109 | 22-Nov-94 | Inbred Corn Line PHHB9; |
| 5,365,014 | 15-Nov-94 | Inbred Corn Line PHMK0; |
| 5,354,942 | 11-Oct-94 | Inbred Corn Line PHEM9; |
| 5,354,941 | 11-Oct-94 | Inbred Corn Line PHEW7; |
| 5,349,119 | 20-Sep-94 | Inbred Corn Line PHTM9; |
| 5,347,081 | 13-Sep-94 | Inbred Corn Line PHK56; |
| 5,347,080 | 13-Sep-94 | Inbred Corn Line PHK74; |
| 5,347,079 | 13-Sep-94 | Inbred Corn Line PHGV6; |
| 5,304,720 | 19-Apr-94 | Inbred Corn Line PHHV4; |
| 5,304,719 | 19-Apr-94 | Inbred Corn Line PHT47; |
| 5,285,004 | 08-Feb-94 | Inbred Corn Line PHBW8; |
| 5,276,265 | 04-Jan-94 | Inbred Corn Line PHR31; |
| 5,245,125 | 14-Sep-93 | Inbred Corn Line PHJ90; |
| 5,220,114 | 15-Jun-93 | Inbred Corn Line PHJ65; |
| 5,159,134 | 27-Oct-92 | Inbred Corn Line PHP55; |
| 5,159,133 | 27-Oct-92 | Inbred Corn Line PHV37; |
| 5,159,132 | 27-Oct-92 | Inbred Corn Line PHR63; |
| 5,157,208 | 20-Oct-92 | Inbred Corn Line PHN73; |
| 5,157,206 | 20-Oct-92 | Inbred Corn Line PHN82; |
| 5,097,096 | 17-Mar-92 | Inbred Corn Line PHW20; |
| 5,097,095 | 17-Mar-92 | Inbred Corn Line PHM10; |
| 5,097,094 | 17-Mar-92 | Inbred Corn Line PHP60; |
| 5,097,093 | 17-Mar-92 | Inbred Corn Line PHJ33; |
| 5,097,092 | 17-Mar-92 | Inbred Corn Line PHR62; |
| 5,095,174 | 10-Mar-92 | Inbred Corn Line PHK35; |
| 5,082,992 | 21-Jan-92 | Inbred Corn Line PHP02; |
| 5,082,991 | 21-Jan-92 | Inbred Corn Line PHN37; |
| 4,812,600 | 14-Mar-89 | Inbred Corn Line PHK29; |
| 4,812,599 | 13-Mar-89 | Inbred Corn Line PHV78; |
| 4,806,669 | 21-Feb-89 | Inbred Corn Line PHK05; |
| 4,806,652 | 21-Feb-89 | Inbred Corn Line PHR25; | and these U.S. patent applications are incorporated by reference.

Once F1 hybrid seed has been obtained, tissue from the seed may be utilized for transformation or the F1 hybrid seed may be germinated and tissue from the F1 plant utilized for transformation. In another embodiment, the F1 may be selfed or crossed with either the recipient or donor parent and F2 or subsequent generations of embryos or tissue utilized in this invention. By "tissue" is intended, for example, embryos, cells, cell suspension cultures, callus, meristems, axillary meristems, leaf discs, and pollen.

The methods of the invention can be practiced with any plant. Such plants include but are not limited to maize (*Zea mays*), canola (*Brassica napus, Brassica rapa* ssp.), alfalfa (*Medicago sativa*), rice (*Oryza sativa*), rye (*Secale cereale*), sorghum (*Sorghum bicolor, Sorghum vulgare*), sunflower (*Helianthus annuus*), wheat (*Triticum aestivum*), soybean (*Glycine max*), tobacco (*Nicotiana tabacum*), potato (*Solanum tuberosum*), peanuts (*Arachis hypogaea*), cotton (*Gossypium hirsutum*), sweet potato (*Ipomoea batatus*), cassava (*Manihot esculenta*), sugar beets (*Beta vulgaris*), millet, oats, barley, wheat, vegetables, ornamentals, *Lupinus albus, Lupinus angustifolius* and conifers. Plants of the present invention may be crop plants (e.g., maize, alfalfa, sunflower, canola, soybean, cotton, peanut, sorghum, wheat, tobacco etc.) and rice. They may also be cereals or forage. Of interest are soybeans, rice, wheat and corn. Corn, in particular, has a number of recalcitrant inbred lines, which have been bred for use in producing hybrids of improved agronomic importance but are difficult to transform. Although it would be beneficial to be able to insert a DNA sequence of interest directly into these inbred lines, transformation in such lines is difficult or a rare event. The present invention provides a means for increasing transformation efficiency as well as reducing the length of time to obtain the gene in a recalcitrant inbred line.

Genes of Interest

Genes of interest are reflective of the commercial markets and interests of those involved in the development of the crop. Crops and markets of interest change, and as developing nations open up world markets, new crops and technologies will emerge also. In addition, as our understanding of agronomic traits and characteristics such as yield and heterosis increases, the choice of genes for transformation will change accordingly. General categories of genes of interest include for example, those genes involved in information, such as zinc fingers, those involved in communication, such as kinases, and those involved in housekeeping, such as heat shock proteins. More specific categories of transgenes, for example, include genes encoding agronomic traits, insect resistance, disease resistance, herbicide resistance, sterility, grain characteristics, and commercial products. Genes of interest include, generally, those involved in oil, starch, carbohydrate, or nutrient metabolism as well as those affecting for example kernel size, sucrose loading, and the like. The quality of grain is reflected in traits such as levels and types of oils, saturated and unsaturated, quality and quantity of essential amino acids, and levels of cellulose.

Grain traits such as oil, starch, and protein content can be genetically altered in addition to using traditional breeding methods. Modifications include increasing content of oleic acid, saturated and unsaturated oils, increasing levels of lysine and sulfur, providing essential amino acids, and also modification of starch. Hordothionin protein modifications are described in U.S. Pat. No. 5,990,389 issued Nov. 23, 1999, U.S. Pat. No. 5,885,801 issued Mar. 23, 1999, U.S. Pat. No. 5,885,802 issued Mar. 23,1999 and U.S. Pat. No. 5,703,049 issued Dec. 30,1997; herein incorporated by reference. Another example is lysine and/or sulfur rich seed protein encoded by the soybean 2S albumin described in U.S. Pat. No. 5,850,016 issued Dec. 15, 1998, and the chymotrypsin inhibitor from barley, Williamson et al. (1987) Eur. J. Biochem. 165:99–106, the disclosures of which are herein incorporated by reference.

Derivatives of the coding sequences can be made by site-directed mutagenesis to increase the level of preselected amino acids in the encoded polypeptide. For example, the gene encoding the barley high lysine polypeptide (BHL) is derived from barley chymotrypsin inhibitor WO98/20133 which is incorporated herein by reference. Other proteins include methionine-rich plant proteins such as from corn (Pedersen et al. (1986) J. Biol. Chem. 261:6279; Kirihara et al. (1988) Gene 71:359; both of which are herein incorporated by reference); and rice (Musumura et al. (1989) Plant Mol. Biol. 12:123, herein incorporated by reference). Other genes encode latex, Floury 2, growth factors, seed storage factors, and transcription factors.

Insect resistance genes may encode resistance to pests that have great yield drag such as rootworm, cutworm, European Corn Borer, and the like. Such genes include, for example *Bacillus thuringiensis* toxic protein genes (U.S. Pat. Nos. 5,366,892; 5,747,450; 5,737,514; 5,723,756; 5,593,881; Geiser et al. (1986) Gene 48:109); lectins (Van Damme et al. (1994) Plant Mol. Biol. 24:825); and the like.

Genes encoding disease resistance traits include detoxification genes, such as against fumonosin (U.S. Pat. No. 5,792,931, issued Aug. 11, 1998); avirulence (avr) and disease resistance genes (Jones et al. (1994) Science 266: 789; Martin et al. (1993) Science 262:1432; Mindrinos et al. (1994) Cell 78:1089); and the like.

Herbicide resistance traits may include genes coding for resistance to herbicides that act to inhibit the action of acetolactate synthase (ALS), in particular the sulfonylurea-type herbicides (e.g., the acetolactate synthase (ALS) gene containing mutations leading to such resistance, in particular the S4 and/or Hra mutations), genes coding for resistance to herbicides that act to inhibit action of glutamine synthase, such as phosphinothricin or basta (e.g., the bar gene), or other such genes known in the art. The bar gene encodes resistance to the herbicide basta, the nptII gene encodes resistance to the antibiotics kanamycin and geneticin, and the ALS gene encodes resistance to the herbicide chlorsulfuron.

Sterility genes can also be encoded in an expression cassette and provide an alternative to physical detasseling. Examples of genes used in such ways include male tissue-preferred genes and genes with male sterility phenotypes such as QM, described in U.S. Pat. No. 5,583,210. Other genes include kinases and those encoding compounds toxic to either male or female gametophytic development.

Commercial traits can also be encoded on a gene or genes that could increase for example, starch for ethanol production, or provide expression of proteins. Another commercial use of transformed plants is the production of polymers and bioplastics such as described in U.S. Pat. No. 5,602,321 issued Feb. 11, 1997. Genes such as B-Ketothiolase, PHBase (polyhydroxybutyrate synthase) and acetoacetyl-CoA reductase (see Schubert et al. (1988) J. Bacteriol. 170:5837–5847) facilitate expression of polyhyroxyalkanoates (PHAs).

Genes of medicinal and pharmaceutical uses, such as that encoding avidin and vaccines or proteins produced utilizing plants as factories are also contemplated as part of this invention.

Gene Targeting

It is recognized that the nucleotide sequence of interest also encompasses nucleotide sequences that may be useful in manipulating the genetic content of a plant, such as sites for insertion of DNA into the genome. Although such nucleotide sequences may not change the phenotype of the plant, the genetic material of the plant will be altered. Insertion or recombination sites for use in the invention are known in the art and include FRT sites (see, for example, Schlake et al. (1994) Biochemistry 33:12746–12751; Huang et al. (1991) Nucleic Acids Res. 19:443–448; Sadowski (1995) Prog. Nuc. Acid Res. Mol. Bio. 51:53–91; Cox (1989) Mobile DNA, ed. Berg and Howe (American Society of Microbiology, Washington D.C.), pp. 116–670; Dixon et al. (1995) 18:449–458; Umlauf et al. (1988) EMBO J. 7:1845–1852; Buchholz et al. (1996) Nucleic Acids Res. 24:3118–3119; Kilby et al. (1993) Trends Genet. 9:413–421; Roseanne et al. (1995) Nat. Med. 1:592–594; Albert et al. (1995) Plant J. 7:649–659; Bailey et al. (1992) Plant Mol. Biol. 18:353–361; Odell et al. (1990) Mol. Gen. Genet. 223:369–378; and Dale et al. (1991) Proc. Natl. Acad. Sci. USA 88:10558–105620; all of which are herein incorporated by reference); and lox (Albert et al. (1995) Plant J. 7:649–659; Qui et al. (1994) Proc. Natl. Acad. Sci. USA 91:1706–1710; Stuurman et al. (1996) Plant Mol. Biol. 32:901–913; Odell et al. (1990) Mol. Gen. Genet. 223: 369–378; Dale et al. (1990) Gene 91:79–85; and Bayley et al. (1992) Plant Mol. Biol. 18:353–361). Such recombination sites, in the presence of a compatible recombinase, allow for the targeted integration of one or more nucleotide sequences of interest into the plant genome.

Non-identical recombination sites that have been introduced into the genome of the recipient plant can be used to establish a target site within a chromosome derived from a recipient plant of the invention for subsequent insertion of one or more nucleotide sequences of interest into the recipient chromosome.

For example, a nucleotide sequence flanked by two non-identical recombination sites is introduced into a chromosome derived from the recipient plant (i.e., a recipient chromosome) thereby establishing a target site for targeted insertion of one or more nucleotide sequences of interest. By "non-identical" recombination sites is intended that the flanking recombination sites are not identical in sequence. That is, one flanking recombination site may be an FRT site where the second recombination site may be a mutated FRT site. The non-identical recombination sites used in the methods of the invention prevent or greatly suppress recombination between the two flanking recombination sites and excision of the nucleotide sequence contained therein. Accordingly, it is recognized that any suitable non-identical recombination sites may be utilized in the invention, including FRT and mutant FRT sites, FRT and lox sites, lox and mutant lox sites, as well as other recombination sites known in the art.

By "suitable" non-identical recombination site is intended that in the presence of active recombinase, excision of sequences between two non-identical recombination sites occurs, if at all, with an efficiency considerably lower than the recombinationally-mediated exchange that targets arrangement of nucleotide sequences into the plant genome. Thus, suitable non-identical sites for use in the invention include those sites where the efficiency of recombination between the sites is low; for example, where the efficiency is less than about 30 to about 50%, or less than about 10 to about 30%, or less than about 5 to about 10%.

In this manner, suitable non-identical recombination sites are introduced into a chromosome derived from a recipient plant from a genetic line of a plant species of interest, establishing a target site for integration of a nucleotide sequence of interest, such as a transgene, into the recipient chromosome. Introduction of the non-identical recombination sites, and hence establishment of the target site, may occur either by traditional breeding practice, such as with cross-pollination techniques, or by direct transformation of the hybrid tissue obtained from an F1 hybrid plant or seed of the invention.

Thus, in one embodiment of the invention, an initial recipient plant chosen from a genetic line of the plant species of interest is sexually crossed with a plant that has within its genome such non-identical recombination sites flanking a selectable marker gene, resulting in a hybrid plant. The plant having the non-identical recombination sites within its genome may be a donor plant of the invention, i.e., one that is selected from a transformation competent genetic line of the same plant species or of another closely related plant species, a plant whose transformation competence is unknown and is chosen from the same plant species or another closely related plant species, or a plant that is recalcitrant to transformation and is chosen from the same plant species or another closely related plant species. The hybrid plant resulting from this sexual cross can then be backcrossed with a second recipient plant from the genetic line of the plant species of interest to obtain progeny. These progeny can then be screened, using methods of this invention, for the presence of the target site (which comprises the non-identical recombination sites flanking the selectable marker gene) integrated into a chromosome derived from the recipient plant. Progeny identified as having the target site integrated into a recipient chromosome can then be used in a traditional breeding approach to introgress, through repeated backcrossing and selection, the selectable marker gene and flanking recombination sites (i.e., the target site) into the genetic line from which the initial recipient plant was chosen.

Thus one can obtain a recipient plant having the recombination sites, and hence the target site for subsequent integration of a nucleotide sequence of interest, incorporated within its genome and having a genetic complement similar to other plants within the genetic line from which the initial recipient plant was chosen. The resulting recipient plant may, however, exhibit the low transformation efficiency that is characteristic of other members of this genetic line. Improved transformation efficiency is then achieved using methods of the invention. In this manner, the resulting recipient plant is crossed with a donor plant as described herein to obtain an F1 hybrid plant or seed of the invention. This F1 hybrid plant or seed comprises the non-identical recombination sites integrated into a chromosome derived from the recipient plant and is characterized by having improved transformation efficiency relative to the recipient plant, or, in some instances, relative to both the recipient plant and the donor plant. The incorporated non-identical recombination sites provide a target site for integration of other nucleotide sequences of interest using a targeting cassette in the presence of a compatible recombinase as described below.

Alternatively, having identified progeny having the target site integrated within a recipient chromosome, one may bypass the introgression step and instead sexually cross the selected progeny with a donor plant of the invention to obtain an F1 hybrid plant or seed of the invention characterized by improved transformation efficiency. As before, the F1 hybrid plant or seed possesses the target site integrated into a recipient chromosome. Targeted integration of one or more nucleotide sequences of interest into the target site of the recipient chromosome is then accomplished using a targeting cassette in the presence of a compatible recombinase as described below. Following targeted integration, the DNA sequences of interest can be introgressed into the genetic line from which the initial recipient plant was chosen, into another genetic line of the same plant species or of another closely related plant species.

In another embodiment of the invention, the target site is established in a recipient chromosome by transformation. In this manner, the hybrid tissue obtained from an F1 hybrid plant or seed of the invention is transformed with a DNA construct comprising the non-identical recombination sites. Thus, for example, using transformation techniques well known in the art, the hybrid tissue is transformed with an expression cassette comprising the non-identical recombination sites, which in turn flank a selectable marker gene. Any selectable marker gene may be used so long as transformed cells can be selected for subsequent culture and plant regeneration. In this way, transformed cells of the hybrid tissue having recombination sites incorporated into the genome are obtained.

It is recognized that any means of transformation may be utilized for inserting the recombination sites. However, *Agrobacterium*-mediated transformation generally tends to insert a lower copy number of transferred DNA than does particle bombardment or other transformation means.

Codon Preference

Where appropriate, the nucleotide sequences of interest that are to be stably integrated into the genome of a recipient plant may be optimized for increased expression in the recipient plant. Where mammalian, yeast, or bacterial genes are used in the invention, they can be synthesized using plant-preferred codons for improved expression. It is recognized that for expression in monocots, dicot genes can also be synthesized using monocot-preferred codons. Methods are available in the art for synthesizing plant-preferred genes. See, for example, U.S. Pat. Nos. 5,380,831, 5,436,391, and Murray et al. (1989) Nucleic Acids Res. 17:477–498, herein incorporated by reference.

The plant-preferred codons may be determined from the codons utilized more frequently in the proteins expressed in the recipient plant of interest. It is recognized that monocot- or dicot-preferred sequences may be constructed as well as plant-preferred sequences for particular plant species. See, for example, EPA 0359472; EPA 0385962; WO 91/16432; Perlak et al. (1991) Proc. Natl. Acad. Sci. USA 88:3324–3328; and Murray et al. (1989) Nucleic Acids Res. 17:477–498; U.S. Pat. Nos. 5,380,831 and 5,436,391; and the like, herein incorporated by reference. It is further recognized that all or any part of the gene sequence may be optimized or synthetic. That is, fully optimized or partially optimized sequences may also be used. Additional sequence modifications are known to enhance gene expression in a cellular host and can be used in the invention. These include elimination of sequences encoding spurious polyadenylation signals, exon-intron splice site signals, transposon-like repeats, and other such well-characterized sequences, which may be deleterious to gene expression. The G-C content of the sequence may be adjusted to levels average for a given cellular host, as calculated by reference to known genes expressed in the host cell. When possible, the sequence may be modified to avoid predicted hairpin secondary mRNA structures.

Thus, for example, where a DNA construct comprising a compatible recombinase gene is to be used for targeted integration of a nucleotide sequence of interest into a target site within a chromosome of interest, the nucleotide sequence encoding the compatible recombinase may be constructed with plant-preferred codons. More particularly, where the gene encodes an FLP recombinase, for example, the FLP gene sequence may be constructed using plant-preferred codons to obtain an FLP recombinase that is optimized for expression in the recipient plant. See "Novel Nucleic Acid Sequence Encoding FLP Recombinase", WO99/27077, which is incorporated by reference.

Transferred DNA

It is recognized that the nucleotide sequences of interest may be utilized in a functional expression unit or cassette. By "functional expression unit" or "cassette" is intended the nucleotide sequence of interest is operably linked with a functional promoter, and in most instances a termination region. There are various ways to achieve the functional expression unit within the practice of the invention. In one embodiment of the invention, the nucleotide sequence of interest is transferred or inserted into the genome as a functional expression unit. Alternatively, the nucleotide sequence may be inserted into a site within the genome that is 3' to a promoter region. In this latter instance, the insertion of the coding sequence 3' to the promoter region is such that a functional expression unit is achieved upon integration.

For convenience, the nucleotide sequences of interest are provided in expression cassettes for expression in the recipient plant. The cassette will include 5' and 3' regulatory sequences operably linked to a nucleotide sequence of interest. By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame. The cassette may additionally contain at least one additional gene or nucleotide sequence of interest to be co-transformed into the plant. Thus, each nucleic acid sequence will be operably linked to 5' and 3' regulatory sequences. Alternatively, the additional gene(s) or nucleotide sequence(s) can be provided on multiple expression cassettes.

Such an expression cassette is provided with a plurality of restriction sites for insertion of the nucleotide sequence of interest that is to be under the transcriptional regulation of the regulatory regions. The expression cassette may additionally contain selectable marker genes.

The expression cassette will include in the 5'-3' direction of transcription, a transcriptional and translational initiation region, a nucleotide sequence of interest, and a transcriptional and translational termination region functional in plants. The transcriptional initiation region, the promoter, may be native or analogous or foreign or heterologous to the plant host. Additionally, the promoter may be the natural sequence or alternatively a synthetic sequence. By "foreign" is intended that the transcriptional initiation region is not found in the native plant into which the transcriptional initiation region is introduced.

While it may be preferable to express the nucleotide sequences of interest using heterologous promoters, the native promoter sequences may be used. Such constructs would change expression levels of any protein encoded by a nucleotide sequence of interest in the plant or plant cell. Thus, the phenotype of the plant or plant cell is altered.

The termination region may be native with the transcriptional initiation region, may be native with the operably linked DNA sequence of interest, or may be derived from another source. Convenient termination regions are available from the potato proteinase inhibitor (PinII) gene or the Ti-plasmid of *A. tumefaciens*, such as the octopine synthase and nopaline synthase termination regions. See also Guerineau et al. (1991) Mol. Gen. Genet. 262:141–144; Proudfoot (1991) Cell 64:671–674; Sanfacon et al. (1991) Genes Dev. 5:141–149; Mogen et al. (1990) Plant Cell 2:1261–1272; Munroe et al. (1990) Gene 91:151–158; Ballas et al. (1989) Nucleic Acids Res. 17:7891–7903; and Joshi et al. (1987) Nucleic Acid Res. 15:9627–9639.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein et al. (1989) PNAS USA 86:6126–6130); potyvirus leaders, for example, TEV leader (Tobacco Etch Virus) (Allison et al. (1986); MDMV leader (Maize Dwarf Mosaic Virus); Virology 154:9–20), and human immunoglobulin heavy-chain binding protein (BiP), (Macejak et al. (1991) Nature 353:90–94); untranslated leader from the coat protein mRNA of alfalfa mosaic virus (AMV RNA 4) (Jobling et al. (1987) Nature 325:622–625); tobacco mosaic virus leader (TMV) (Gallie et al. (1989) in Molecular Biology of RNA, ed. Cech (Liss, N.Y.), pp. 237–256); and maize chlorotic mottle virus leader (MCMV) (Lommel et al. (1991) Virology 81:382–385). See also, Della-Cioppa et al. (1987) Plant Physiol. 84:965–968. Other methods known to enhance translation can also be utilized, for example, introns, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

Generally, the expression cassette will comprise a selectable marker gene for the selection of transformed cells or tissues. See generally, Yarranton (1992) Curr. Opin. Biotech. 3:506–511; Christopherson et al. (1992) Proc. Natl. Acad. Sci. USA 89:6314–6318; Yao et al. (1992) Cell 71:63–72; Reznikoff (1992) Mol. Microbiol. 6:2419–2422; Barkley et al. (1980) Operon, pp. 177–220; Hu et al. (1987) Cell 48:555–566; Brown et al. (1987) Cell 49:603–612; Figge et al. (1988) Cell 52:713–722; Deuschle et al. (1989) Proc. Natl. Acad. Sci. USA 86:5400–5404; Fuerst et al. (1989) Proc. Natl. Acad. Sci. USA 86:2549–2553; Deuschle et al. (1990) Science 248:480–483; M. Gossen (1993) Ph.D dissertation, University of Heidelberg; Reines et al. (1993) Proc. Natl. Acad. Sci. USA 90:1917–1921; Labow et al. (1990) Mol. Cell Bio. 10:3343–3356; Zambretti et al. (1992) Proc. Natl. Acad. Sci. USA 89:3952–3956; Baim et al. (1991) Proc. Natl. Acad. Sci. USA 88:5072–5076; Wyborski et al. (1991) Nucleic Acids Res. 19:4647–4653; Hillenand-Wissman (1989) Topics in Mol. and Struc. Biol. 10:143–162; Degenkolb et al. (1991) Antimicrob. Agents Chemother. 35:1591–1595; Kleinschnidt et al. (1988) Biochemistry 27:1094–1104; Gatz et al. (1992) Plant J. 2:397–404; A. L. Bonin (1993) Ph.D. dissertation, University of Heidelberg; Gossen et al. (1992) Proc. Natl. Acad. Sci. USA 89:5547–5551; Oliva et al. (1992) Antimicrob. Agents Chemother. 36:913–919; Hlavka et al. (1985) Handbook of Exp. Pharmacology 78; Gill et al. (1988) Nature 334:721–724. Such disclosures are herein incorporated by reference.

Transformation

Once the tissue is obtained from the F1 hybrid plant or seed, the nucleotide sequences of interest can be introduced in the plant by any method known in the art. In this manner, genetically modified plants, plant cells, plant tissue, seed, and the like can be obtained. Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) Biotechniques 4:320–334), electroporation (Riggs et al. (1986) Proc. Natl. Acad. Sci. USA 83:5602–5606, *Agrobacterium*-mediated transformation (Townsend et al., U.S. Pat No. 5,563,055), direct gene transfer (Paszkowski et al. (1984) EMBO J. 3:2717–2722), and ballistic particle acceleration (see, for example, Sanford et al., U.S. Pat. No. 4,945,050; Tomes et al. (1995) "Direct DNA Transfer into Intact Plant Cells via Microprojectile Bombardment," in Plant Cell, Tissue, and Organ Culture: Fundamental Methods, ed. Gamborg and Phillips (Springer-Verlag, Berlin); and McCabe et al. (1988) Biotechnology 6:923–926). Also see Weissinger et al. (1988) Ann. Rev. Genet. 22:421–477; Sanford et al. (1987) Particulate Science and Technology 5:27–37 (onion); Christou et al. (1988) Plant Physiol. 87:671–674 (soybean); McCabe et al. (1988) Bio/Technology 6:923–926 (soybean); Finer and McMullen (1991) In Vitro Cell Dev. Biol. 27P:175–182 (soybean); Singh et al. (1998) Theor. Appl. Genet. 96:319–324 (soybean); Datta et al. (1990) Biotechnology 8:736–740 (rice); Klein et al. (1988) Proc. Natl. Acad. Sci. USA 85:4305–4309 (maize); Klein et al. (1988) Biotechnology 6:559–563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in Plant Cell, Tissue, and Organ Culture: Fundamental Methods, ed. Gamborg (Springer-Verlag, Berlin) (maize); Klein et al. (1988) Plant Physiol. 91:440–444 (maize); Fromm et al. (1990) Biotechnology 8:833–839 (maize); Hooykaas-Van Slogteren et al. (1984) Nature (London) 311:763–764; Bowen et al., U.S. Pat. No. 5,736,369 (cereals); Bytebier et al. (1987) Proc. Natl. Acad. Sci. USA 84:5345–5349 (Liliaceae); De Wet et al. (1985) in The Experimental Manipulation of Ovule Tissues, ed. Chapman et al. (Longman, New York), pp. 197–209 (pollen); Kaeppler et al. (1990) Plant Cell Reports 9:415–418 and Kaeppler et al. (1992) Theor. Appl. Genet. 84:560–566 (whisker-mediated transformation); D'Halluin et al. (1992) Plant Cell 4:1495–1505 (electroporation); Li et al. (1993) Plant Cell Reports 12:250–255 and Christou and Ford (1995) Annals of Botany 75:407–413 (rice); Osjoda et al. (1996) Nature Biotechnology 14:745–750 and U.S Pat. 5,981,840 (maize via *Agrobacterium tumefaciens*); all of which are herein incorporated by reference.

Another useful basic transformation protocol involves a combination of wounding by particle bombardment, followed by use of *Agrobacterium* for DNA delivery, as described by Bidney et al., Plant Mol. Biol. 18:301–31 (1992). Useful plasmids for plant transformation include pBin 19. See Bevan, Nucleic Acids Research 12:8711–8721 (1984), and hereby incorporated by reference. This method is preferred for transformation of sunflower plants.

In general, the intact meristem transformation method involves imbibing seed for 24 hours in the dark, removing the cotyledons and root radical, followed by culturing of the meristem explants. Twenty-four hours later, the primary leaves are removed to expose the apical meristem. The explants are placed apical dome side up and bombarded, e.g., twice with particles, followed by co-cultivation with *Agrobacterium*. To start the co-cultivation for intact meristems, Agrobacterium is placed on the meristem. After about a 3-day co-cultivation period the meristems are transferred to culture medium with cefotaxime plus kanamycin for the NPTII selection.

The split meristem method involves imbibing seed, breaking of the cotyledons to produce a clean fracture at the plane of the embryonic axis, excising the root tip and then bisecting the explants longitudinally between the primordial leaves. The two halves are placed cut surface up on the medium then bombarded twice with particles, followed by co-cultivation with *Agrobacterium*. For split meristems, after bombardment, the meristems are placed in an *Agrobacterium* suspension for 30 minutes. They are then removed from the suspension onto solid culture medium for three day co-cultivation. After this period, the meristems are transferred to fresh medium with cefotaxime plus kanamycin for selection.

Many transformation protocols may be used in the practice of the invention to transform a tissue obtained from the hybrid plant with one or more nucleotide sequences of interest, although protocols producing single copy events work better with this invention. Preferably the transformation protocol is the same protocol, or a protocol that has minor modifications, as the protocol used in transformation of tissues obtained from the donor plant. This protocol yields a useful level of transformation efficiency in tissues obtained from either the F1 hybrid plant or seed, or from the donor plant. For example, if the donor plant is Hi-II, the tissue from the hybrid plant will be transformed using the standard protocol for Hi-II transformation, or a minor modification thereof. This strategy not only yields a useful level of transformation efficiency, it also allows for the use of the same protocol generally regardless of the genetic line used as the source of the recipient plant, making transformation of multiple genetic lines a more efficient process.

Once the DNA sequence of interest has been introduced into tissue from the hybrid plant, transformed cells are selected and transgenic plants regenerated using methods well known in the art. See, for example, McCormick et al. (1986) Plant Cell Reports 5:81–84; WO97/41228 and U.S. Pat. No. 5,981,840, which are incorporated by reference.

For those hybrid tissues engineered to have a target site, i.e., non-identical recombination sites, within a recipient chromosome, use of a targeting cassette in the presence of a compatible recombinase as described above results in insertion of the nucleotide sequence of interest within a recipient chromosome. In this case, plants regenerated from transformed cells will have the nucleotide sequence of interest inserted within a recipient chromosome. Thus, these transformed cells that also test positive for transformation with the nucleotide sequence of interest may be directly transferred to plant regeneration media, since those have the transferred DNA in the recipient chromosome.

For those hybrid tissues not having target sites incorporated within a recipient chromosome, plants regenerated from transformed cells will have approximately a 50:50 chance of having the nucleotide sequence of interest inserted within a recipient chromosome. In this case, it is preferable, though not required, to have an early round of selection that discriminates between those transformation events having the nucleotide sequence of interest inserted within a recipient chromosome and those events having the sequence inserted within a donor chromosome. In this manner, only those transformation events identified as having the nucleotide sequence inserted within a recipient chromosome using chromosome localization methods described above are carried forward for regeneration into plants.

These regenerated transgenic plants may then be grown to maturity and sexually crossed with the same transformed strain ("selfed"), or "backcrossed" with another recipient plant chosen from the genetic line from which the initial recipient plant was chosen to obtain transgenic plants having desired characteristics of the recipient plant. Alternatively, the regenerated transgenic plants may use to "introgress" the nucleotide sequence of interest into another genetic line of the same plant species or into a genetic line of another closely related plant species. In this manner, it is possible to produce a transgenic plant and obtain transgenic seed for a genetic line that is characterized by low transformation efficiency.

Cloning Flanking DNA

A variety of techniques able to distinguish two DNAs are contemplated in this invention. Genomic DNA is isolated and used to identify the flanking DNA through cloning as in plasmid rescue, library screening, PCR-based techniques or any method that obtains or identified at least some of the polynucleotides of the flanking region. Utilization of the flanking DNA, compared with other methods, provides a greater efficiency and speed with which the parental chromosome can be identified.

Methods for isolating genomic DNA from organism are known to those of ordinary skill in the art. While the methods of the invention do not depend on any particular method for isolating genomic DNA, it is recognized that the choice of isolation method will depend on a variety of factors including, the species of organism, the age of the organism, the specific cells or tissues selected and the intended use of the genomic DNA. Methods for the isolation of genomic DNA are generally known in the art and are disclosed in Sambrook et al. (1989) Molecular Cloning: A Laboratory Manual ($2^{nd}$ ed., Cold Spring Harbor Laboratory Press, Plainview, N.Y.) and in The Maize Handbook (1994) pp517–653; Springer-Verlag New York, which are incorporated by reference.

1. Plasmid Rescue

The principles of plasmid rescue for isolating genomic sequences flanking transferred DNA can be found in Behringer and Medford (1992) Plant Mol. Biol. Rept. 10:190–198 and Feldmann (1992) "T-DNA insertion mutagenesis in Arabidopsis seed infection/transformation," in Methods in *Arabidopsis* Research, ed. Koncz et al. (London: World Scientific), pp. 274–289. The presence of the antibiotic marker gene, amp, from the transformed plasmid backbones in the events made it possible to isolate flanking sequences via this approach. This approach was also used because plasmid-rescue procedures are generally not sensitive, compared with PCR-based cloning methods, to the presence of structural rearrangements of transgenic DNA.

2. Inverse PCR

The principles of inverse PCR for isolating genomic sequences flanking a known or unknown transferred DNA sequence (e.g. transgenes and transposons) can be found in Gasch et al. (1992) "Gene isolation with the polymerase chain reaction," Methods in *Arabidopsis* Research, ed. Koncz et al. (London: World Scientific), pp. 342–356, and Britt and Earp (1994) "The polymerase chain reaction: applications to maize transposable elements," in The Maize Handbook, ed. Freeling and Walbot (Springer-Verlag, New York), pp. 586–592. In the present study, sequences flanking transgenic DNA from transgenic mi1ps events were obtained by using an inverse-PCR technique.

Methods for determining chromosomal location of DNA sequences of interest are known in the art. See, for example, Leitch et al. (1996) in Plant Molecular Biology, ed. Clark (Springer-Verlag, Berlin), pp. 461–519, for a discussion regarding localization of DNA sequences, and the use of sequential hybridizations with specific gene probes and genomic in situ hybridization for allocating transgene insertion events to a parental genome. One such approach entails the use of Genome Walker™ kit sold by Clontech Laboratories, Inc., Palo Alto, Calif. cloning or PCR of the genomic DNAs flanking the DNA construct of interest, followed by sequencing or DNA hybridization and methods known in the art to determine whether the flanking DNA is of donor or recipient parent genomic origin. See particularly the copending entitled "Methods for Identifying Desired Transgenic Organisms" U.S. application Ser. No. 09/696,621, which is incorporated by reference in its entirety.

The flanking DNA can be used to identify the parental origin of the chromosome containing the transferred DNA. This can be done through comparison of the F1 hybrid plant, the recipient plant and the donor plant using for example sequence analysis, Southern analysis, gel electrophoresis, RFLP, SNP or other means of identification or combinations thereof.

One embodiment includes isolating genomic DNA and digesting with at least one restriction enzyme. Compatible adapters are ligated to the digested genomic DNA, followed by PCR amplification employing two primers, one designed to hybridize to a nucleotide sequence within the adapter and the other designed to hybridize to a nucleotide sequence within the transgene. The expected product of such a PCR amplification is a DNA molecule containing a portion of the transgene and flanking DNA. The nucleotide sequence of the PCR product can be determined and used to design PCR primers and hybridization probes specific to the portion of flanking DNA in the PCR product. Alternatively, the PCR product can be labeled, during or after amplification, for use as a hybridization probe. Genomic DNA is then isolated from an ancestor of the transgenic plant and the PCR product is used directly or indirectly to determine if the transgene integrated into DNA originating in the donor plant or recipient plant by any means known to those of ordinary skill in the art. Typically, such means include a comparison of results obtained with genomic DNA from one or more ancestors and genomic DNA from the F1 hybrid plant.

Figure 7:
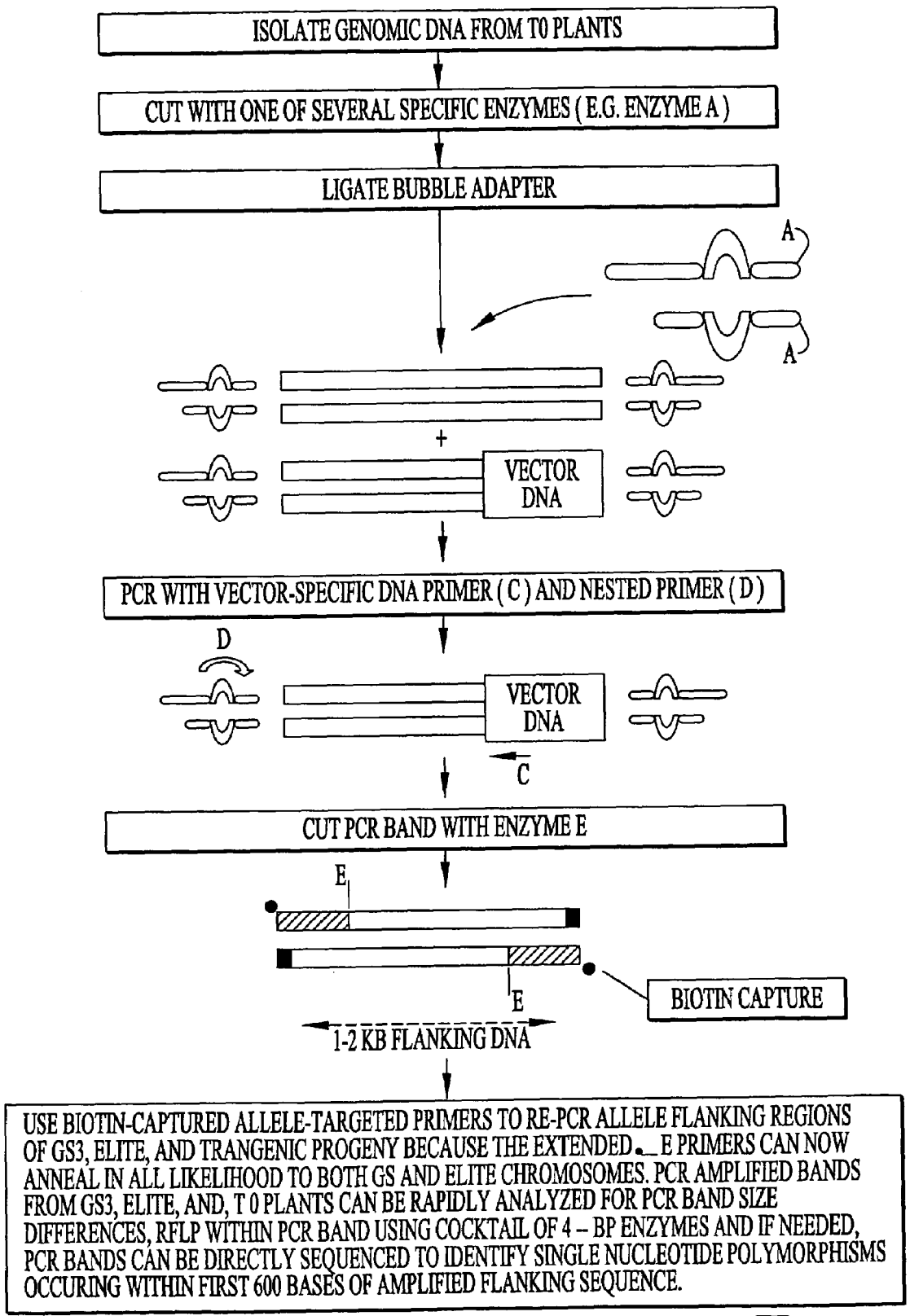

In another embodiment, restriction digested genomic DNA of a transformed plant is ligated with bubble adapters (FIG. 7). The ligated genomic DNA is PCR amplified employing two ligand-labeled primers, one complementary to the bubble region of the bubble adapter and the other complementary to the transferred DNA. While any ligand known to those of ordinary skill in the art can be employed to label the primers, the preferred ligand of the present invention is biotin. Methods of synthesizing and using ligand-labeled primers are known to those of ordinary skill in the art. The PCR product is digested with a restriction enzyme that cleaves the PCR product into at least three fragments. Then the ligand-labeled DNA fragments are isolated by methods known to those of ordinary skill in the art such as, for example, affinity chromatography. Preferably, single-stranded, ligand-labeled fragments are isolated. The single-stranded, ligand-labeled fragments are then used as primers in separate PCR amplification of genomic DNA from the F1 hybrid plant and one or both parents. The resulting products of the separate PCR amplifications are compared to determine the parental origin of the flanking DNA.

If the transferred DNA contains a selectable marker gene for use in microorganisms such as bacteria and yeast, plasmid rescue can be employed instead of inverse PCR. The product of inverse PCR or the "rescued" plasmid can be used as a hybridization probe for Southern blotting of restriction enzyme-digested genomic DNA of the F1 hybrid plant and one or both parents. Or the product can be analyzed through sequencing, enzyme restriction analysis or other molecular comparison means.

The methods of the invention involve identifying at least one base pair difference between the donor parent and the recipient parent in the flanking DNA. It may be necessary to identify more than one distinct DNA fragment comprising flanking DNA.

While certain embodiment of the invention comprise isolating genomic DNA from a parent, it is recognized that parental genomic DNA sequences may have already been determined. It is also recognized that other ancestors may substitute for the donor and recipient parents.

For example, in one embodiment, the initial recipient plant from the genetic line of a plant species of interest is crossed with a donor plant that to obtain an F1 hybrid plant or seed of the invention. Hybrid tissue obtained from this F1 hybrid plant or seed, which has improved transformation efficiency, can then be transformed with a DNA construct comprising one or more nucleotide sequences of interest. Transformed cells of the hybrid tissue identified as having the transferred DNA within a recipient chromosome are determined at this point by methods of this invention and carried forward. In this manner, transformed hybrid tissue having the nucleotide sequence or sequences of interest integrated within a donor chromosome is obtained. Following regeneration of the transformed hybrid tissue, the resulting transformed plant can then be backcrossed with a second recipient plant from the genetic line from which the initial recipient plant was chosen to obtain progeny. Those progeny comprising the nucleotide sequence of interest within a recipient chromosome can then be selected for subsequent use in introgressing the nucleotide sequence of interest into the genetic line from which the initial recipient plant was chosen, into another genetic line of the plant species of interest, or into a genetic line of another closely related plant species of interest. Progeny may also be selfed.

For example, in one embodiment, the initial recipient plant from the genetic line of a plant species of interest is crossed with a donor plant that comprises the target site integrated within its genome to obtain an F1 hybrid plant or seed of the invention comprising the target site integrated within a donor chromosome. Hybrid tissue obtained from this F1 hybrid plant or seed, which has improved transformation efficiency, can then be transformed with a DNA construct comprising one or more nucleotide sequences of interest using a targeting cassette in the presence of a compatible recombinase as described below. In this manner, transformed hybrid tissue having the nucleotide sequence or sequences of interest integrated within a donor chromosome is obtained. Following regeneration of the transformed hybrid tissue, the resulting transformed plant can then be backcrossed with a second recipient plant from the genetic line from which the initial recipient plant was chosen to obtain progeny. Those progeny comprising the nucleotide sequence of interest within a recipient chromosome can then be selected for subsequent use in introgressing the nucleotide sequence of interest into the genetic line from which the initial recipient plant was chosen, into another genetic line of the plant species of interest, or into a genetic line of another closely related plant species of interest.

Having established a target site integrated within a chromosome of interest, which may be a donor chromosome in some embodiments or a recipient chromosome in other embodiments described herein, nucleotide sequences of interest can be targeted for insertion into the target site using a targeting cassette as described below. In the presence of a compatible recombinase, the non-identical recombination sites in the chromosome of interest provide a means of moving desired genes or nucleotide sequences from the targeting cassette into the chromosome at the location of the target site.

It is recognized that the chromosome of interest may comprise multiple target sites; i.e., sets of non-identical recombination sites. In this manner, multiple manipulations of the target site in the plant are available. By "target site" in the plant is intended the DNA sequence that has been inserted into a chromosome of interest and which comprises the non-identical recombination sites. Preferably the target site has been established within a recipient chromosome so that integration of the nucleotide sequence of interest can be directed to a recipient chromosome.

In one embodiment of the invention, a hybrid tissue obtained from an F1 hybrid plant or seed of the invention contains at least one target site integrated into a chromosome derived from the recipient plant. The target site is characterized by being flanked by non-identical recombination sites as previously defined.

By "targeting cassette" is intended a DNA construct comprising one or more nucleotide sequences of interest flanked by identical or non-identical recombination sites corresponding to those non-identical recombination sites contained in the target site of the chromosome of interest. By "compatible recombinase" is intended a recombinase that recognizes the non-identical recombination sites and catalyzes site-specific recombination. Thus, introduction of the targeting cassette in the presence of a compatible recombinase results in exchange of the nucleotide sequence flanked by the non-identical recombination sites of the target site with the nucleotide sequences of interest from the targeting cassette such that the nucleotide sequences of interest now reside on the chromosome of interest. In one embodiment of the invention, introduction of the targeting cassette in the presence of a compatible recombinase results in targeted integration of a nucleotide sequence of interest into a recipient chromosome within the genome of an F1 hybrid plant or seed of the invention.

The targeting cassette may be introduced into a plant comprising the target site integrated within its genome either by traditional breeding methods or by transformation. Thus, for example, in one embodiment of the invention, an F1 hybrid plant or seed comprising a target site integrated within its genome, preferably within a recipient chromosome, is sexually crossed with a plant comprising the targeting cassette integrated within its genome. The latter plant may be from the same plant species as the F1 hybrid or from another closely related plant species. The resulting progeny have a target site and a targeting cassette integrated within their genome. In the presence of an active compatible recombinase, the nucleotide sequence of interest flanked by the non-identical sites of the targeting cassette is integrated into the target site residing on the recipient chromosome. In this manner, nucleotide sequences of interest may be "moved" between chromosomes of different parental origin. This is of value when positional effects influence expression of the nucleotide sequence of interest.

Alternatively, the targeting cassette may be introduced into the plant genome using transformation techniques known in the art. Thus, tissue obtained from a plant comprising the target site integrated within its genome, preferably within a recipient chromosome, may be transformed with a DNA construct comprising the targeting cassette. Again, in the presence of a compatible recombinase, the nucleotide sequence of interest flanked by the non-identical sites of the targeting cassette is integrated into the target site residing on the chromosome of interest, preferably a recipient chromosome.

It is recognized that the compatible recombinase can be provided by any means known in the art. That is, it can be provided in a plant cell by transforming the plant with an expression cassette capable of expressing the recombinase in the plant, by transient expression, or by providing messenger RNA (mRNA) for the recombinase or the recombinase protein.

In one embodiment, hybrid tissue obtained from an F1 hybrid plant or seed of the invention is cotransformed with a DNA construct comprising the targeting cassette and with a DNA construct comprising the compatible recombinase gene operably linked to an inducible promoter. Use of an inducible promoter allows for tight regulation of recombinase expression such that insertion of the nucleotide sequences of interest into the target site is predictable and stably maintained. In this manner, the recombinase catalyzes insertion of the nucleotide sequences of interest into the target site in response to a stimulus, such as a chemical or environmental stimulus.

As noted above, the non-identical recombination sites in the targeting cassette correspond to those in the target site of the chromosome of interest. That is, if the target site of the chromosome of interest contains flanking non-identical recombination sites of FRT and a mutant FRT, the targeting cassette will contain the same FRT and mutant FRT non-identical recombination sites.

It is furthermore recognized that the particular recombinase used in the invention will depend upon the non-identical recombination sites in the target site of the chromosome of interest and the targeting cassette. That is, if FRT sites are utilized, the FLP recombinase will be needed. In the same manner, where lox sites are utilized, the Cre recombinase is required. If the non-identical recombination sites comprise both an FRT and a lox site, both the FLP and Cre recombinase will be required in the plant cell to bring about the recombination event.

The FLP recombinase is a protein that catalyzes a site-specific reaction that is involved in amplifying the copy number of the 2-$\mu$ plasmid of *Saccharomyces cerevisiae* during DNA replication. FLP protein has been cloned and expressed. See, for example, Cox (1993) Proc. Natl. Acad. Sci. USA 80:4223–4227, herein incorporated by reference. The FLP recombinase for use in the invention may be that derived from the genus *Saccharomyces*. It may be preferable to synthesize the recombinase using plant-preferred codons for optimum expression in a plant of interest. The bacteriophage recombinase Cre catalyzes site-specific recombination between two lox sites. The Cre recombinase is known in the art. See, for example, Guo et al. (1997) Nature 389:40–46; Abremski et al. (1984) J. Biol. Chem. 259: 1509–1514; Chen et al. (1996) Somat. Cell Mol. Genet. 22:477–488; and Shaikh et al. (1977) J. Biol. Chem. 272: 5695–5702; herein incorporated by reference. The Cre recombinase may also be synthesized using plant-preferred codons.

It is recognized that many variations of the targeted insertion aspect of the invention can be practiced. See for example WO9925821; WO9925855; WO9925840; herein incorporated by reference.

Thus the methods of the invention provide a means for transformation of recipient plants with nucleotide sequences of interest, regeneration of transgenic recipient plants comprising nucleotide sequences of interest, and targeted integration of nucleotide sequences of interest into a chromosome derived from a recipient plant. The methods are particularly useful for obtaining transgenic recalcitrant inbreds having the nucleotide sequences of interest integrated within a chromosome derived from a recalcitrant inbred.

All publications and patent applications mentioned in this specification are herein incorporated by reference to the same extent as if each individual publication or patent application was specifically and individually indicated to be incorporated by reference.

The following examples are offered by way of illustration and not by way of limitation.

EXPERIMENTAL

Example 1

Embryogenic Response and Transformability of Hi-II X Elite Hybrid Immature Embryos Crosses were made between Hi-II, a highly transformable genotype, and several recalcitrant elite inbred lines, to generate hybrid immature embryos. Hybrid immature embryos were collected approximately 10 DAP and utilized immediately for transformation using *Agrobacterium* as a transformation vector. *Agrobacterium*-mediated transformation protocol for Hi-II is as follows. All culture media are presented in the Appendix.

Preparation of *Agrobacterium*

The engineered *Agrobacterium tumefaciens* LBA4404 was constructed as per U.S. Pat. No. 5,591,616 to contain a gene of interest and a selectable marker gene, typically BAR (D'Halluin et al. (1992) Methods Enzymol. 216:415–426) or PAT (Wohlleben et al. (1988) Gene 70:25–37).

To use the engineered vector in plant transformation, a master plate of single bacterial colonies was first prepared by inoculating the bacteria on minimal AB medium and then incubating the bacteria plate inverted at 28° C. in darkness for about 3 days. A working plate was then prepared by selecting a single colony from the plate of minimal A medium and streaking it across a plate of YP medium. The YP-medium bacterial plate was then incubated inverted at 28° C. in darkness for 1–2 days.

*Agrobacterium* for plant transfection and co-cultivation was prepared 1 day prior to transformation. About 30 ml of minimal A medium in a flask containing 50 µg/ml spectinomycin was inoculated with a ⅛ loopful of *Agrobacterium* from a 1–2-day-old working plate. The *Agrobacterium* was then grown at 28° C. at 200 rpm in darkness overnight (about 14 hours). In mid-log phase, the *Agrobacterium* was harvested and resuspended at 3 to $5 \times 10^8$ CFU/ml in 561Q medium+100 µM acetosyringone using standard microbial techniques and standard curves.

Immature Embryo Preparation

Nine to ten days after controlled pollination of a corn plant, developing immature embryos are opaque and 1–1.5 mm long and are the appropriate size for Agro-infection. The husked ears were sterilized in 50% commercial bleach and 1 drop Tween for 30 minutes, and then rinsed twice with sterile water. The immature embryos were aseptically removed from the caryopsis and placed into 2 ml of sterile holding solution comprised of 561Q+100 µM acetosyringone.

*Agrobacterium* Infection and Co-Cultivation of Embryos

Holding solution was decanted from excised immature embryos and replaced with prepared *Agrobacterium*. Following gentle mixing and incubation for about 5 minutes, the *Agrobacterium* was decanted from the immature embryos. Immature embryos were then moved to a plate of 562P medium, scutellum surface upwards, and incubated at 20° C. for 3 days in darkness followed by incubation at 28° C. for 3 days in darkness (see U.S. Pat. No. 5,981,840).

Selection of Transgenic Events

Following incubation, the immature embryos were transferred to 563O medium for selection of events. The transforming DNA possesses a herbicide-resistance gene, for example the BAR gene, which confers resistance to bialaphos. At 10- to 14-day intervals, embryos were transferred to 563O medium. Actively growing putative transgenic embryogenic tissue was visible in 6–8 weeks.

Regeneration of $T_0$ Plants

Transgenic embryogenic tissue was transferred to 288W medium and incubated at 28° C. in darkness until somatic embryos matured, or about 10 to 18 days. Individual matured somatic embryos with well-defined scutellum and coleoptile were transferred to 272 embryo germination medium and incubated at 28° C. in the light. After shoots and roots emerged, individual plants were potted in soil and hardened-off using typical horticultural methods.

Confirmation of Transformation

Putative transgenic events were subjected to analysis to confirm their transgenic nature. The specific analytical test performed on any transgenic was dependent on the transgene.

For example, almost all events were tested for the presence of the gene of interest by PCR amplification. In those events produced with A B.T. gene, an ELISA was performed on leaf tissue from the regenerated plants. And in those events produced with the GUS gene, tissues were stained with GUS histochemical reagent. Additionally, $T_0$ plants were painted with bialaphos herbicide (1% v/v Liberty™). The subsequent lack of a herbicide-injury lesion indicated the presence and action of the BAR/PAT transgene, which conditions for herbicide resistance.

Results

Hybrid immature embryos derived from crosses between Hi-II X proprietary elites can be cultured successfully and transformed using a Hi-III/*Agrobacterium* protocol in a genotype-independent fashion.

Culture Responses of Hybrid Immature Embryos

A high frequency and vigorous embryogenic response was achieved from hybrid embryos of Hi-II and the proprietary recalcitrant elite inbreds tested when cultured on a medium typically used for Hi-II (288) (Table 1). The frequency of embryogenic response was generally greater when Hi-II was the female. The preponderance of type I or type II response varied between genotypes and among embryos within a genotype, but immature embryos across all genotypes possessed sectors of both tissue phenotypes.

Embryogenic cultures of hybrid immature embryos were serially propagated, and were visually selected to propagate with a friable phenotype. Plants were regenerated from these embryogenic cultures and produced progeny seed.

TABLE 1

CULTURE RESPONSE OF HYBRID EMBRYOS
(% OF EMBRYOS PRODUCING EMBRYOGENIC TISSUE)

| ELITE | Cross | | |
|---|---|---|---|
| GENOTYPE | X Hi-II | Hi-II X | REGENERABLE |
| PHTE4 | 70 | 82 | Y |
| PHP18 | 54 | 65 | Y |
| PH05F | 71 | 90 | Y |
| PH09B | NT* | 81 | Y |
| PHJ90 | 59 | 78 | Y |
| PH24E | 84 | 38 | Y |
| PHN46 | 43 | 54 | Y |
| PH21T | 77 | 43 | Y |
| PHAA0 | NT* | 78 | Y |
| ASKC27 | NT* | 92 | Y |

*NT = not tested

Transformation of Hybrid Immature Embryos

Transgenic events were produced from hybrid immature embryos of Hi-II X PHN46 and reciprocals, and Hi-II X PHP18 and reciprocals utilizing the Agrobacterium transformation vector and protocol described above. The frequency of transformation was about double when Hi-II was the female, in contrast to the reciprocal, in both PHN46 and PHP18 combinations (Table 2). Transformation frequency was measured as a function of the number of immature embryos that produced a confirmed transgenic event. Considered individually (not as hybrids), PHN46 and PHP18 display transformation frequencies of about 0.5% (throughput of about 70). Throughput is measured as independent events/year/person that can be produced. The optimal transformation protocol for the two elites is not the same as that utilized for Hi-II. In this example, throughput for the hybrid immature embryos is increased many fold.

TABLE 2

TRANSFORMATION OF Hi-II X
ELITE HYBRID IMMATURE EMBRYOS

| ELITE GENOTYPE and TRANSGENE | TRANSFORMATION FREQUENCY (throughput) | |
|---|---|---|
| | X Hi-II | Hi-II X |
| PHP18/ubi::B.T. GENE | 4.2 (540) | 9.4 (1204) |
| PHN46/glb1::mi1ps::glb1 | 7.9 (1020) | 12.4 (1593) |

The distribution of event phenotype, type I versus type II, revealed that type II events occurred with a greater frequency when Hi-II was the female (Table 3).

TABLE 3

DISTRIBUTION OF EVENT PHENOTYPE

| PEDIGREE | COUNT OF EVENT PHENOTYPES (frequency) | |
|---|---|---|
| | I | II |
| Hi-II X PHP18/ubi::B.T. GENE | 8 (0.25) | 24 (0.75) |
| PHP18 X Hi-II/ubi::B.T. GENE | 2 (0.50) | 2 (0.50) |
| Hi-II X PHN46/glb1::mi1ps::glb1 | 25 (0.50) | 25 (0.50) |
| PHN46 X Hi-II/glb1::mi1ps::glb1 | 18 (0.78) | 5 (0.22) |

Example 2

*Agrobacterium*-Mediated Transformation of Hi-II (Female) X Elite (Male) Hybrid Immature Embryos Transformation of a broad range of proprietary elite genotypes was pursued with Hi-II as the female only. Transgenic events were produced from hybrid immature embryos of Hi-II X proprietary elite inbred crosses utilizing the standard Hi-II/*Agrobacterium* transformation protocol described in Example 1. In most all cases, confirmed transgenic events were recovered from the hybrids at a frequency and throughput significantly greater than for the comparable inbreds alone (Table 4).

TABLE 4

TRANSFORMATION OF Hi-II X ELITE HYBRID IMMATURE EMBRYOS

| Hi-II X ELITE/ TRANSFORMATION VECTOR | HYBRID | | TRANSFORMATION |
|---|---|---|---|
| | TRANSFORMATION EFFICIENCY (%) | THROUGHPUT (independent events/year/person) | EFFICIENCY (%) (AND THROUGHPUT) OF ELITE PARENT ALONE |
| PHT05/ubi:ubiint::GUS::pinII | 39.9 | 5109 | 0 (0) |
| PH21T/ubi:ubiint::GUS::pinII | 19.2 | 2464 | ? |
| PHP02/ubi:ubiint::GUS::pinII | 17.6 | 2255 | 0.14 (18) |
| ASKC27/glb1::mi1ps::glb1 | 9.1 | 1165 | ? |
| PH24E/ubi:ubiint::GUS::pinII | 9.0 | 1165 | 0 (0) |
| PH05F/ubi:ubiint::GUS::pinII | 8.0 | 1032 | ? |
| PHP18/ubi:ubiint::GUS::pinII | 5.4 | 694 | 0.55 (70) |
| PHN46/ubi:ubiint::GUS::pinII | 2.4 | 307 | 0.57 (73) |
| PHN46/glb1::mi1ps::glb1 | 12.0 | 1700 | |
| PHN46/glb1::AGP2tr::glb1 | 18.0 | 2600 | |
| PHN46/gz::Ht12ss:BHL3n::gz | 6.0 | 870 | |
| PH09B/ubi:ubiint::GUS::pinII | 0.27 | 34 | 0.61 (78) |
| PH09B/ubi:ubiint::GUS::pinII | 42.3 | 6000 | |
| PHAA0/ubi:ubiint::GUS::pinII | 0.28 | 36 | 0.13 (16) |
| Hi-II control | 23.5 | 3032 | NA |

? = Unknown or untested
NA = not applicable

Example 3

Culture Response and Transformability of Hybrid Immature Embryos Obtained from Crosses between Several Transformable and Recalcitrant Elite Inbred Genotypes Crosses were made between Hi-II or A188, another transformable maize genotype, and various elite inbred lines such as Dabo-1, Dabo-2, and Dabo-12. Culture response and transformability using particle-gun transformation or *Agrobacterium*-mediated transformation were examined in inbred immature embryos and hybrid immature embryos obtained from crosses between inbreds and elite inbreds. *Agrobacterium*-mediated transformation was performed as in Example 1. Particle-gun transformation protocol was as follows.

Preparation of Target Tissue

Immature maize embryos were isolated from ears 9–11 days after pollination using a scalpel. Prior to isolation the ears were surface sterilized in 30% Chlorox bleach plus 0.5% Micro detergent for 20 minutes, and rinsed two times with sterile water. The immature embryos were excised and placed embryo axis side down (scutellum side up), 25 embryos per plate, on 560Y medium for 4 hours and then aligned within the 2.5-cm target zone in preparation for bombardment.

Preparation of DNA

Plasmid vectors containing Ubi:ubi int:Gus:PinII or 35S: Bar:pinII were made. This Gus plasmid DNA plus plasmid DNA containing a Bar selectable marker were precipitated onto 1.1 µm (average diameter) tungsten pellets using a $CaCl_2$ precipitation procedure as follows:

100 µl prepared tungsten particles in water 10 µl (1 µg) DNA in TrisEDTA buffer (1 µg total)

100 µl 2.5 M $CaCl_2$

10 µl 0.1 M spermidine

Each reagent was added sequentially to the tungsten particle suspension, while maintained on the multitube vortexer. The final mixture was sonicated briefly and allowed to incubate under constant vortexing for 10 minutes. After the precipitation period, the tubes were centrifuged briefly, liquid removed, washed with 500 ml 100% ethanol, and centrifuged for 30 seconds. Again the liquid was removed, and 105 µl 100% ethanol was added to the final tungsten particle pellet. For particle gun bombardment, the tungsten/DNA particles were briefly sonicated and 10 µl spotted onto the center of each macrocarrier and allowed to dry about 2 minutes before bombardment.

Particle Gun Treatment

The sample plates were bombarded at level #3 in particle gun #HE34-1 or #HE34-2. All samples received a single shot at 650 PSI, with a total of ten aliquots taken from each tube of prepared particles/DNA.

Subsequent Treatment

Following bombardment, the embryos were kept on 560Y medium for 2 days, and then examined for transient GUS expression or transferred to 560R selection medium containing 3 mg/liter Bialaphos, and subcultured every 2 weeks. After approximately 10 weeks of selection, selection-resistant callus clones were transferred to 288J medium to initiate plant regeneration. Following somatic embryo maturation (2–4 weeks), well-developed somatic embryos were transferred to medium for germination and transferred to the lighted culture room. Approximately 7–10 days later, developing plantlets were transferred to 272V hormone-free medium in tubes for 7–10 days until plantlets were well established. Plants are then transferred to inserts in flats (equivalent to 2.5" pot) containing potting soil and grown for 1 week in a growth chamber, subsequently grown an additional 1–2 weeks in the greenhouse, then transferred to classic 600 pots (1.6 gallon) and grown to maturity. Transformed plant tissues were assessed for stable expression of GUS.

Results

Callus was examined for type I, type II, or mixed type I-type II phenotype. As seen in Table 5, the inbred A188 UM showed the highest percentage of type II phenotype, the inbred AP84 showed the highest percentage of type I phenotype, and the inbreds Dabo-1 and Dabo-12 showed the highest percentage of mixed type I-type II phenotype. Among the hybrids, Hi-II showed the highest percentage of type II phenotype, while the hybrid cross AP84 X PHN46 showed the highest percentage of type I phenotype.

TABLE 5

CALLUS PHENOTYPE OF SEVERAL MAIZE INBREDS AND HYBRIDS (TYPE I/TYPE II/MIXED TYPE I AND TYPE II)

| Female | Selves | PHN46 | AP84 | A188 |
|---|---|---|---|---|
| A188 | 68.5/0/23 | 72.5/0/0 | 85/8.4/0 | |
| A188 UM | 0/100/0 | 47.5/0/5 | 46/38/6 | |
| A188 IFS | 24/12/0 | | | |
| A188 JT | 27.5/8/0 | 93.8/1.25/0 | 100/0/0 | |
| Hi-II | 0/89/0 | 5/91.2/3.8 | 0/84/0 | |
| Dabo-1 | 17.6/6.8/59.6 | 90.5/0/0 | | 43/28.1/20.3 |
| Dabo-2 | 0/87.2/12.3 | | | |
| Dabo-12 | 23.3/16.7/43.3 | 100/0/0 | | |
| AP84 | 91/0/0 | 100/0/0 | | |

Transient and stable GUS expression were measured as described elsewhere (see Jefferson (1987) Plant Mol. Biol. Rep. 5:387–405) following staining of embryo or plant tissue with X-Gluc staining solution (McCabe et al. (1988) Bio/Technology 6(87):923–926) for 12 h at 37° C. in the dark. Transient and stable expression data are shown in Tables 6 and 7, respectively.

TABLE 6

TRANSIENT GUS EXPRESSION (%) FROM AGROBACTERIUM-MEDIATED AND PARTICLE GUN TRANSFORMATION EVENTS AND WITH DIFFERENT MAIZE GENOTYPES

| Female | Selves (gun/Agro) | PHN46 (gun/Agro) | AP84 (gun/Agro) | A188 (gun/Agro) |
|---|---|---|---|---|
| A188 | 7.5/25 | 1/0 | 60/19.50 | |
| A188 UM | 50/20 | 25/0 | 3/40 | |
| A188 IFS | 35/35 | | | |
| A188 JT | 4.75/55 | 34/2 | 62.5/42 | |
| Hi-II | 5.25/65 | 21/17.50 | 22/13 | |
| Dabo-1 | 43.25/16.5 | 32.5/8 | | 43/12 |
| Dabo-2 | 32.75/11 | | | |
| Dabo-12 | 28.5/10.5 | 75/4.5 | | |
| AP84 | 2/13.25 | 85/1.5 | | |

TABLE 7

STABLE GUS EXPRESSION (%) FROM PARTICLE GUN (Gun) AND AGROBACTERIUM-MEDIATED (Agro) TRANSFORMATION EVENTS AND WITH DIFFERENT MAIZE GENOTYPES

| Female | Selves (Gun %/Agro %) | PHN46 (Gun %/Agro %) | AP84 (Gun %/Agro %) | A188 (Gun %/Agro %) |
|---|---|---|---|---|
| A188 | 4.25/0 | 4.3/0 | 7.4/1.05 | |
| A188 UM | 4.9/0 | 2.3/3.2 | 0/4.55 | |
| A188 IFS | 3.15/0 | | | |
| A188 JT | 3.4/0 | 12.7/5 | 8.7/2.85 | |
| Hi-II | 0/1 | 2.05/0 | 10/0 | |
| Dabo-1 | 4.12/0 | 0/0 | | 4.7/1.7 |
| Dabo-2 | 0/0 | | | |
| Dabo-12 | 0/0 | 5.3/0 | | |
| AP84 | 0/1 | 7.5/0 | | |

These data indicate that A188 inbreds and Dabo inbreds showed similar transformation efficiency of about 4% with particle-gun transformation. Of the hybrid crosses, A188JT X HG11 and A188JT X AP84 showed the highest transformation efficiency with both particle gun and *Agrobacterium*-mediated transformation. The best overall hybrid genotypes of those tested for transformation efficiency were A188JT X PHN46 (12.7%) for particle gun transformation, and A188JT X PHN46 (5.0%) and A188UM X AP84 (4.55%) for *Agrobacterium*-mediated transformation.

Example 4

Identification of Ancestral Origin of Transgenic Chromosomes

Transgenic Materials

Two types of transgenic materials were used in the present study to test whether or not flanking sequences of a transgene can be reliably used to identify parental origins of transgenic chromosomes in the F1 hybrid transformation system.

The first type of material was generated by co-bombardment of immature maize embryos of the genotype Hi-II with two plasmids, one carrying a gene of interest, hordothionin (Ht12) (U.S. Pat. Nos. 5,885,801 and 5,885,802 issued Mar. 23, 1999 and WO9940209; all incorporated by reference herewithin) and the other carrying a selectable marker gene, pat or bar. Hordothionin is a synthetic gene that encodes the hordothionin protein containing a high level of lysine and thus has nutrition value in the feed industry. Regenerated transformed ($T_0$) plants from the transformed Hi-II embryos were crossed to a Pioneer elite inbred line, PHN46, and the resulting transgenic F1 hybrid progeny (Hi-II X PHN46) were used in this study. Since the Ht12 genes in those events were originally transformed into Hi-II chromosomes, we can use these materials to demonstrate whether or not determination of parental origins of transgenic chromosomes via genomic sequences flanking transgenes is affected by the presence of chromosomes from other parental lines in future crossing generations.

The other type of material used in the present study was generated by transformation with the milps gene along with a selectable marker gene, pat, through *Agrobacterium*-mediated transformation (PHP6). Milps is one of the genes involved in the biochemical pathways of inositol phosphate synthesis (see WO99/05298, incorporated by reference). The gene was introduced into immature F1 hybrid maize embryos obtained from the cross of Hi-II with the elite inbred PHN46 (Hi-II X PHN46) and the resulting transformed ($T_0$) plants were used in this study. Since the transgenes were directly transformed into F1 hybrid chromosomes, it was unknown into which parental chromosome the transgene was integrated in these events.

Plant DNA Extraction and Southern Hybridization

Isolation of plant genomic DNA, enzyme restriction digestion, agarose gel electrophoresis, Southern blotting and hybridization were performed according to Zhong et al. (1999) "Commercial production of aprotinin in transgenic maize seeds," Mol. Breed. 5:345–356.

Cloning Genomic Flanking Sequences of a Transgene
1. Plasmid Rescue

In the present study, genomic sequences flanking transgenic Ht12 DNAs from the events TC1 (co-transformed with plasmids PHP9 and PHP7) and TC0 (co-transformed with plasmids PHP1 and PHP8) were isolated through the plasmid-rescue approach (Behringer and Medford (1992), and Feldmann (1992) supra).

TC1 and TC0 DNA was digested with the restriction enzymes NsiI and EcoRI, respectively, at 37° C. for 6 hrs. Restriction enzymes were chosen for digestion in such a way that the length of fragments released from integrated plasmid DNA was technically desirable for self-ligation and the origin of replication and amp gene from the plasmid backbones were kept intact. The digestion products were circularized by self-ligation according to the procedures described in the Clontech manufacture user manual (Clontech Laboratories, Inc., Palo Alto, Calif.). The circular DNA molecules were then transformed into *E. coli* following the conditions of the Gibco BRL manufacture manual and the transformed cells were selected on bacterial medium with 70–100 ng/µl ampicillin.

Those that survived over ampicillin selection on medium were further amplified and subjected to restriction and sequencing analyses to determine whether or not the selected clones carried a host DNA sequence adjunct to transgenic DNA.

2. Inverse PCR

Sequences flanking transgenic DNA from transgenic milps events were obtained by using an inverse-PCR technique (Gasch et al. (1992), Britt and Earp (1994), supra).

DNA from transgenic plants was digested with the restriction enzyme NheI, which had only one restriction site in the T-DNA. The digestion products were circularized by self-ligation following the same ligation procedures described above for plasmid rescue. The circularized DNAs were amplified with a pair of divergent transgene-based primers and the products from the first round of PCR were further amplified with a second set of primers that were nested within the first set of primers. Amplified PCR products were subjected to restriction and sequencing analyses to determine whether or not they contained a host-plant DNA sequence.

Identification of Transgenic Chromosomes in F1 Hybrids

When there is a parental restriction fragment length (RFLP) or single nucleotide polymorphism (SNP) in the genomic regions closely flanking a transgene, it is possible to use the polymorphism information to determine which parental chromosome(s) the transgene is integrated into.

RFLP analysis followed the Southern protocols described earlier. The genomic sequences flanking transgenic DNA were used as probes to reveal the restriction patterns of both parents and transgenic hybrids. If an RFLP marker(s) that is present in one of the two parents, parent A for example, is replaced by a new RFLP marker(s) in their transgenic hybrid, the transgene must be located on a chromosome from the parent A.

SNP analysis was accomplished by comparing the profiles of flanking sequences from both parents and their transgenic hybrids. Sequence profiles from transgenic hybrids should match that from one of the parents, by which a parental transgenic chromosome can be determined. Sequence analysis was carried out on an ABI Prism 377 sequencer manufactured by Perkin Elemer.

Verification of the Flanking Sequence in Identification of Chromosome Identity of Parent 1. Cloning Genomic sequences Flanking Transgenic DNA in TC1 and TC0

Genomic sequence flanking transgenic Ht12 DNA were isolated from the events TC1 and TC0 by using a plasmid-rescue approach. As explained earlier, the events were generated by particle bombardment in Hi-II background and crossed to a Pioneer inbred line PHN46. Several self-ligated clones from NsiI or EcoRI digested trangenic DNA survived over antibiotic selection from both events. Two clones, designated as 19-2 and 28, were respectively obtained from TC1 and TC0 and were selected for further analyis. The clones 19-2 and 28 were about 5 Kb and 3.2 Kb long, respectively. Restriction enzyme anyalsis confirmed that the original cloning sites were retained in the clones. Further anyalsis revealed that at least one restriction site that was not in either of the two co-transformed plasmids was present in the clones. This strongly suggested the existence of a stretch of non-plasmid DNA sequence in the clones selected.

2. Determination of the Parental Origins of the Transgenic Chromosomes in TC1 and TC0 Events To verify that the Ht12 was originally transformed into a Hi-II chromosome in TC1, RFLP profiles of Hi-II, PHN46, and TC1 were compared. DNA samples from those lines were digested with the restriction enzyme BamHI and probed with a 700 bp non-plasmid DNA fragment isolated from the clone 19-2. Hi-II and PHN46 each showed a single hybridized band but the Hi-II's hybridized fragment (about 7 kb) was much larger than that of PHN46 (about 1.0 kb) Two hybridization fragments were observed in TC1. One of them was equivalent in size to that of PHN46 while the other was smaller than that of Hi-II (6.5 kb vs. 7 kb). No corresponding Hi-II fragment was observed in Tc1. These results suggested that the Ht12 gene in TC1 must have originally integrated into a Hi-II chromosome, which agreed with the known fact described above.

The transgenic DNA on a Hi-II chromosome in TC0 was confirmed through SNP analysis. The SNP profiles in the genomic regions flanking the transgenic DNA among Hi-II, PHN46, and TC0 were obtained. A total of 6 SNPs were observed between Hi-II and PHN46 in the amplified PCR products. The sequencing profile of TC0 was the same as that of Hi-II, confirming that the transgenic DNA was integrated into a Hi-II chromosome in TC0.

Identification of the Parental Origins of Transgenic Chromosomes in Hi-IIxPHN46 F1 Hybrids 1. Cloning Genomic Sequences Flanking Transgenes in Transgenic Hi-II X PHN46 F1 Hybrids Inverse-PCR technique was used to clone genomic sequences flanking transgenic mi1ps expression cassettes in Hi-II X PHN46 F1 hybrids. Sequences contiguous to the right borders of T-DNA were obtained from more than 10 mi1ps events. In most cases, a second PCR was necessary to obtain specific amplification of a desired PCR product. The length of flanking sequences cloned from the study varied, ranging from below 200 bp up to more than 1 kb long.

2. Determination of the Parental Origins of Transgenic Chromosomes in mi1ps Events Parental origins of transgenic chromosomes in 6 mi1ps events (Table 8) were determined, two by Southern blot and four by SNP analyses, in this study. The hybridization patterns of Hi-II, PHN46, and the F1 transgenic mi1ps event 2482.53-1-12A were determined. The DNA samples were digested by the restriction enzyme NheI and the blot was probed with a flanking sequence isolated from the transgenic event 2482.53-1-12A. Hi-II showed two hybridized bands (1.4 and 0.6 kbs) that were also present in the F1 transgenic hybrid 2482.53-1-12A. Three hybridization bands were observed in PHN46 and one of them (0.6 kb) was also present in both Hi-II and 2482.53-1-12A. The two other PHN46 bands (1.5 and 1.1 kbs) were not present in 2482.53-1-12A. Instead, they were replaced by a novel band (6.0 kb) in 2482.53-1-12A. These results suggest that the mi1ps gene in 2482.53-1-12A integrated into a PHN46 chromosome.

TABLE 8

CLONED GENOMIC SEQUENCES FLANKING MI1PS EXPRESSION CASSETTES AND THEIR USES IN IDENTIFYING THE PARENTAL ORIGINS OF TRANSGENIC CHROMOSOMES IN SIX TRANSGENIC F1 HYBRID EVENTS

| Event Code | Gene of Interest | Transformation Method | Transformation Target | Parental Origin of Transgenic Chromosomes |
|---|---|---|---|---|
| 2482.53-1-1 | MI1PS | Agrobacterium | F1, Hi-IIxPHN46 | PHN46 |
| 2482.53-1-8 | MI1PS | Agrobacterium | F1, Hi-IIxPHN46 | Hi-II |
| 2482.53-1-12A | MI1PS | Agrobacterium | F1, Hi-IIxPHN46 | PHN46 |
| 2482.53-1-12B | MI1PS | Agrobacterium | F1, Hi-IIxPHN46 | PHN4 |
| 2482.53-1-3 | MI1PS | Agrobacterium | F1, Hi-IIxPHN46 | Hi-II |
| 2482.53-1-5 | MI1PS | Agrobacterium | F1, Hi-IIxPHN46 | Hi-II |

Example 5

Biolistics Transformation of Immature Embryos of Hi-II x PHN46, a Proprietary Elite Inbred Preparation of Target Tissue Ears from reciprocal crosses of Hi-II and PHN46 were produced from greenhouse or field grown plants. Ears were harvested based on developmental stage of the immature embryo and used when the embryo becomes opaque about 8–13 DAP, depending on genotype and environmental conditions.

The ears were surface sterilized in 50% Clorox bleach+ 0.5% Micro detergent for 20 minutes, and rinsed 2× with sterile water. Immature embryos were aseptically dissected from sterilized ears and placed embryo axis side down (scutellum side up) on 560L in Petri dishes and cultured in darkness at 28° C. After 4–5 days the embryos were transferred to 560Y for 4 hours, arranged within the 2 cm target zone at 10 embryos per plate. The embryos were oriented with the coleorhizal end pointing up at approximately a 30° angle.

Particle Gun Bombardments

Particles and DNA were associated as described below in Particle-DNA Association. The target plates were bombarded at shelf 2 (8.2 cm from rupture disk) in PDS-1000 following the manufacturers recommendations. Immature embryos received a single bombardment at 650 PSI at 28° C. in Hg vacuum.

Selection of Transformants

Following bombardment, the embryos remained on 560Y for 2 days in darkness at 28° C. The embryos were then transferred to 560R selection medium containing 3 mg/liter bialaphos and cultured in darkness at 28° C. The embryos were transferred to fresh medium of the same composition every 10–14 days.

Six to twelve weeks following bombardment, bialaphos-resistant embryogenic tissue were produced from the immature embryos. The tissues from individual embryos were identified as putative transgenic events and were individually subcultured and propagated on 560R. Analysis to document the transgenic nature of the herbicide-resistant events was carried out at this stage.

Fragments of embryogenic tissue from events chosen for regeneration were subcultured 288J maturation medium in 100×25 plates. The tissue was grown in darkness at 28° C. After about 10–14 days, matured somatic embryos were individually transferred to 272V, germination medium, in 100×25 Petri plates and maintained at 28° C. in light. Approximately 7–10 days later, developing plants were transferred to 272V medium in 150×25 mm culture tubes and incubated for 7–10 days until roots were well-formed and new aerial growth is well-established.

Plants were then transferred to inserts in flats (equivalent to 2.5" pot) containing potting soil and grown for 1 week in a humidified growth chamber. The flats of regenerated plants were grown an additional 1–2 weeks in the greenhouse for hardening-off. Finally, individual regenerated plants were transplanted to 1.6 gallon pots and grown to maturity.

Particle Preparation and Particle-DNA Association

Preparation of Tungsten Particles
1) Weigh 60 mg 1u GE W particles into 15 ml centrifuge tube.
2) Add 2 ml 0.1M $HNO_3$ and sonicate on ice for 20 minutes.
3) Withdraw acid, add 1 ml sterile deionized water and transfer sample to a 2 ml Sarstedt tube. Sonicate briefly.
4) Centrifuge to pellet particles
5) Withdraw water and add 1 ml 100% EtOH. Sonicate briefly.
6) Centrifuge to pellet particles
7) Withdraw EtOH and add 1 ml 100% EtOH. Sonicate briefly.
8) Centrifuge to pellet particles
9) Withdraw EtOH and add 1 ml sterile deionized water. Sonicate. Pipet 250 ml of suspension into 4, 2 ml tubes. Add 750 ml of sterile deionized water to each tube. Freeze tungsten sample between uses.

Particle/DNA Association—CaCl2/Spermidine Method
1) 100 ul prepared 1 u W particles dispensed into siliconized tube
2) 10 ul (1 ug total) plasmid DNA in TE buffer
3) 100 ul 2.5 M $CaCl_2$
4) 10 ul 0.1 M spermidine Each reagent is added sequentially to the particle suspension with gentle vortexing. After addition of all components, the preparation was vortexed at a setting #3–4 for ten minutes. After the association period, the tubes were centrifuged briefly, the supernatant decanted, and the particle-DNA amalgam was washed with 500 ml 100% ethanol, and the particles were pelleted by centrifugation for 30 seconds in a microfuge. The supernatant was removed, and the particle-DNA association is resuspended in 105 ul 100% ethanol. Prior to bombardment, the associated particles-DNA were briefly sonicated and 10 ul of the suspension was spotted onto the center of each macro-carrier and allowed to dry for approximately 2 minutes before bombardment.

Results:

Production of Transformants

Transgenic events were produced from embryos derived from reciprocal crosses of Hi-II and PHN46 using construct PHP6A (gz::HT12::gz)+PHP0 (ubi::PATmo::pinII). The events were confirmed by PCR reaction for the agronomic gene of interest (gz::HT12::gz). In this comparison, the production of transgenic events via particle gun is documented, as well as using Hi-II as the female in the production of the hybrid target embryos.

TABLE 9

| Genotype | Transformation Frequency |
| --- | --- |
| Hi-II X PHN46 | 4.5% |
| PHN46 X Hi-II | 2.3% |

Example 6

Seed Production from Hybrid Transformants

Transgenic events were produced from a variety of hybrids of Hi-II X proprietary elite inbred using proprietary commercially valuable gene constructs in an Agrobacterium vector. $T_0$ plants were regenerated and established in a greenhouse to recover progeny $T_1$ seed.

The performance of $T_0$ plants from hybrid transformants was measured by plant survival to reproductive maturity and seed production. Comparisons were made relative to Hi-II transformants alone. Comparisons were conducted with $T_0$'s that occupied the greenhouse contemporaneously. In these comparisons, the survival and seed production of transgenic events derived from hybrids far surpassed the performance of Hi-II transformants.

TABLE 10

Performance of $T_0$ Plants from Hybrid Transformants

Survival and Average Seed

| $T_0$ Genotype | % $T_0$ Pollinated and Harvested | Average Seed per $T_0$ |
|---|---|---|
| Hi-II | 67 | 85.4 |
| HYBRID (pooled) | 85 | 131.4 |
| selfed | | 121.5 |
| crossed | | 174.3 |

Distribution of Seed Production
$T_0$ Genotype

| $T_0$ Seed Count | Hi-II | Hybrid selfed | Hybrid crossed |
|---|---|---|---|
| >20 | 66 | 74 | 90 |
| >40 | 58 | 65 | 81 |
| >60 | 50 | 61 | 75 |

Percentage of Occurrence

Example 7

Dicots

Crosses are made between a soybean variety that is a particular transformable line, such as "Jack", and a recalcitrant, commercially desirable line such as Pioneer 93B82. F1 embryos of Jack x 93B82 are transformed using biolistics techniques with embryogenic cultures derived from immature embryos (see Klein et al. (1987) Nature (London) 327:70; WO0032782; and WO0028058, which are incorporated by reference).

Following bombardment, selection for transformed events is performed and transformed plant tissues are tested for stable expression of one or more transgenes. Transgenic tissue is used for isolation of plant genomic DNA, enzyme restriction digestion, agarose gel electrophoresis, Southern blotting and hybridization as described in Zhong et al, supra, and as known in the art.

Genomic DNA containing flanking sequences of the F1 transformed event and that from one or more parents are isolated and may be cut with restriction enzymes and/or sequenced. Transgenic chromosomes are identified as described in previous examples.

TABLE 11

561 Q

| Ingredient | Amount | Unit |
|---|---|---|
| D-I Water, Filtered | 950.000 | ml |
| Chu (N6) Basal Salts (Sigma C-1416) | 4.000 | g |
| Eriksson's Vitamin Mix (1000x Sigma-1511) | 1.000 | ml |
| Thiamine.HCL.4 mg/ml | 1.250 | ml |
| 2,4-D 0.5 mg/ml (No. 2A) | 3.000 | ml |
| L-proline | 0.690 | g |
| Sucrose | 68.500 | g |
| Glucose | 36.000 | g |

TABLE 11-continued

561 Q

| Ingredient | Amount | Unit |
|---|---|---|

Directions
# = Add after sterilizing
Dissolve ingredients in polished D-I $H_2O$ in sequence
Adjust pH to 5.2 w/KOH
Q.S. to volume with polished D-I $H_2O$ after adjusting pH
Filter sterilize (do not autoclave)

TABLE 12

562 P

| Ingredient | Amount | Unit |
|---|---|---|
| D-I Water, Filtered | 950.000 | ml |
| Chu (N6) Basal Salts (Sigma C-1416) | 4.000 | g |
| Eriksson's Vitamin Mix (1000x Sigma-1511) | 1.000 | ml |
| Thiamine.HCL.4 mg/ml | 1.250 | ml |
| 2,4-D 0.5 mg/ml | 4.000 | ml |
| L-proline | 0.690 | g |
| Sucrose | 30.000 | g |
| Gelrite @ | 3.000 | g |
| Silver Nitrate 2 mg/ml # | 0.425 | ml |
| Aceto Syringone 100 mM # | 1.000 | ml |

Directions
@ = Add after Q.S. to volume
# = Add after sterilizing and cooling to temperature
Dissolve ingredients in polished D-I $H_2O$ in sequence
Adjust pH to 5.8 w/KOH
Q.S. to volume with polished D-I $H_2O$ after adjusting pH
Sterilize and cool to 60° C.

TABLE 13

563 O

| Ingredient | Amount | Unit |
|---|---|---|
| D-I Water, Filtered | 950.000 | ml |
| Chu (N6) Basal Salts (Sigma C-1416) | 4.000 | g |
| Eriksson's Vitamin Mix (1000x Sigma-1511) | 1.000 | ml |
| Thiamine.HCL.4 mg/ml | 1.250 | ml |
| Sucrose | 30.000 | g |
| 2,4-D 0.5 mg/ml (No. 2A) | 3.000 | ml |
| L-proline | 0.690 | g |
| Mes Buffer | 0.500 | g |
| Agar (Sigma A-7049, Purified) @ | 8.000 | g |
| Silver Nitrate 2 mg/ml # | 0.425 | ml |
| Bialaphos 1 mg/ml # | 3.000 | ml |
| Agribio Carbenicillin 50 mg/ml # | 2.000 | ml |

Directions
@ = Add after Q.S. to volume
# = Add after sterilizing and cooling to temperature
Dissolve ingredients in polished D-I $H_2O$ in sequence
Adjust to pH 5.8 w/koh
Q.S. to volume with polished D-I $H_2O$ after adjusting pH
Sterilize and cool to 60° C.

TABLE 14

288 W

| Ingredient | Amount | Unit |
|---|---|---|
| D-I $H_2O$ | 950.000 | ml |
| MS Salts | 4.300 | g |
| Myo-Inositol | 0.100 | g |
| MS Vitamins Stock Solution (No. 36J) | 5.000 | ml |
| Zeatin.5 mg/ml | 1.000 | ml |
| Sucrose | 60.000 | g |

TABLE 14-continued

288 W

| Ingredient | Amount | Unit |
| --- | --- | --- |
| Agar (Sigma A-7049, Purified) @ | 8.000 | g |
| IAA 0.5 mg/ml # | 2.000 | ml |
| .1 Mm ABA # | 1.000 | ml |
| Bialaphos 1 mg/ml # | 3.000 | ml |
| Agribio Carbenicillin 50 mg/ml # | 2.000 | ml |

Directions  
@ = Add after Q.S. to volume  
# = Add after sterilizing and cooling to temperature  
Dissolve ingredients in polished D-I H$_2$O in sequence  
Adjust to pH 5.6  
Q.S. to volume with polished D-I H$_2$O after adjusting pH  
Sterilize and cool to 60° C.  
Add 3.5 g/L of Gelrite for cell biology

TABLE 15

272

| Ingredient | Amount | Unit |
| --- | --- | --- |
| D-I H$_2$O | 950.000 | ml |
| MS Salts | 4.300 | g |
| Myo-Inositol | 0.100 | g |
| MS Vitamins Stock Solution | 5.000 | ml |
| Sucrose | 40.000 | g |
| Gelrite @ | 1.500 | g |

Directions  
@ = Add after Q. S to volume  
Dissolve ingredients in polished D-I H$_2$O in sequence  
Adjust to pH 5.6  
Q.S. to volume with polished D-I H$_2$O after adjusting pH  
Sterilize and cool to 60° C.

TABLE 16

272 V

| Ingredient | Amount | Unit |
| --- | --- | --- |
| D-I H$_2$O | 950.000 | Ml |
| MS Salts (GIBCO 11117-074) | 4.300 | G |
| Myo-Inositol | 0.100 | G |
| MS Vitamins Stock Solution ## | 5.000 | Ml |
| Sucrose | 40.000 | G |
| Bacto-Agar @ | 6.000 | G |

Directions:  
@ = Add after bringing up to volume  
Dissolve ingredients in polished D-I H$_2$O in sequence  
Adjust to pH 5.6  
Bring up to volume with polished D-I H$_2$O after adjusting pH  
Sterilize and cool to 60° C.  
## = Dissolve 0.100 g of Nicotinic Acid; 0.020 g of Thiamine.HCL; 0.100 g of Pyridoxine.HCL; and 0.400 g of Glycine in 875.00 ml of polished D-I H$_2$O in sequence. Bring up to volume with polished D-I H$_2$O. Make in 400 ml portions. Thiamine.HCL & Pyridoxine.HCL are kept in a dark desiccator. Store for one month, unless contamination or precipitation occurs, then make fresh stock.  
Total Volume (L) = 1.00

TABLE 17

288 J

| Ingredient | Amount | Unit |
| --- | --- | --- |
| D-I H$_2$O | 950.000 | Ml |
| MS Salts | 4.300 | g |
| Myo-Inositol | 0.100 | g |

TABLE 17-continued

288 J

| Ingredient | Amount | Unit |
| --- | --- | --- |
| MS Vitamins Stock Solution ## | 5.000 | ml |
| Zeatin .5 mg/ml | 1.000 | ml |
| Sucrose | 60.000 | g |
| Gelrite @ | 3.000 | g |
| Indoleacetic Acid 0.5 mg/ml # | 2.000 | ml |
| 0.1 mM Abscisic Acid | 1.000 | ml |
| Bialaphos 1 mg/ml # | 3.000 | ml |

Directions:  
@ = Add after bringing up to volume  
Dissolve ingredients in polished D-I H$_2$O in sequence  
Adjust to pH 5.6  
Bring up to volume with polished D-I H$_2$O after adjusting pH  
Sterilize and cool to 60° C.  
Add 3.5g/L of Gelrite for cell biology.  
## = Dissolve 0.100 g of Nicotinic Acid; 0.020 g of Thiamine.HCL; 0.100 g of Pyridoxine.HCL; and 0.400 g of Glycine in 875.00 ml of polished D-I H$_2$O in sequence. Bring up to volume with polished D-I H$_2$O. Make in 400 ml portions. Thiamine.HCL & Pyridoxine.HCL are in Dark Desiccator. Store for one month, unless contamination or precipitation occurs, then make fresh stock.  
Total Volume (L) = 1.00

TABLE 18

560 R

| Ingredient | Amount | Unit |
| --- | --- | --- |
| D-I Water, Filtered | 950.000 | ml |
| CHU (N6) Basal Salts (SIGMA C-1416) | 4.000 | g |
| Eriksson's Vitamin Mix (1000X SIGMA-1511) | 1.000 | ml |
| Thiamine.HCL 0.4 mg/ml | 1.250 | ml |
| Sucrose | 30.000 | g |
| 2,4-D 0.5 mg/ml | 4.000 | ml |
| Gelrite @ | 3.000 | g |
| Silver Nitrate 2 mg/ml # | 0.425 | ml |
| Bialaphos 1 mg/ml # | 3.000 | ml |

Directions:  
@ = Add after bringing up to volume  
# = Add after sterilizing and cooling to temp.  
Dissolve ingredients in D-I H$_2$O in sequence  
Adjust to pH 5.8 with KOH  
Bring up to volume with D-I H$_2$O  
Sterilize and cool to room temp.  
Total Volume (L) = 1.00

TABLE 19

560 Y

| Ingredient | Amount | Unit |
| --- | --- | --- |
| D-I Water, Filtered | 950.000 | ml |
| CHU (N6) Basal Salts (SIGMA C-1416) | 4.000 | g |
| Eriksson's Vitamin Mix (1000X SIGMA-1511) | 1.000 | ml |
| Thiamine.HCL 0.4 mg/ml | 1.250 | ml |
| Sucrose | 120.000 | g |
| 2,4-D 0.5 mg/ml | 2.000 | ml |
| L-Proline | 2.880 | g |
| Gelrite @ | 2.000 | g |
| Silver Nitrate 2 mg/ml # | 4.250 | ml |

Directions:  
@ = Add after bringing up to volume  
# = Add after sterilizing and cooling to temp.  
Dissolve ingredients in D-I H$_2$O in sequence  
Adjust to pH 5.8 with KOH  
Bring up to volume with D-I H$_2$O  
Sterilize and cool to room temp.  
Autoclave less time because of increased sucrose  
Total Volume (L) = 1.00

Example 8

Sunflower Hybrids

When SMF3 was used as a pollen recipient, the plants were bagged to prevent cross pollination and to isolate the flowers. This was done by utilizing a finely meshed plastic Delnet bag, and placing the bag on the developing flower bud at the R4 stage prior to flowering. To emasculate the plants, since they would be fertile and pollen producing, at the flowering stage, anthers were removed by tweezers on a daily basis. After removal, the plants would then be washed to insure that no pollen persisted on the flowering head. This process would be done early each morning before pollen would dehisce from the anthers, to further reduce any chance of selfing. This emasculation process would go on for several days until all of the flowers within the composite head would have opened. This normally takes 5–7 days.

When commercial sunflower lines were used, the female lines were made up of both sterile and fertile genotypes. The sterile lines (F designation) have cytoplasmically controlled sterility which prevents pollen shedding. The CMS (cytoplasmic male sterility) was identified and developed by an interspecific cross or *Helianthus annuus* and *H. petiolaris*. The fertile lines consisted of both maintainers (G designation) and restorers (M designation) of the CMS genotypes. The same emasculation process was used as indicated above.

Hybrids were made by collecting pollen from the SMF3 or from other genotypes, using small papers. The papers then were used to cross the pollen on to the genetically or emasculated sterile plants.

Sunflower Transformation

A general method for transformation of sunflower meristem tissues is practiced as follows (see also European patent number 486233, herein incorporated by reference, and Malone-Schoneberg, J., et al., Plant Science, 103:199–207 (1994)).

Mature sunflower seed (*Helianthus annuus* L.) of elite line hybrids or research selection SMF-3 (a selection of USDA germplasm release SFM-3; cms/*H. petiolaris* Nuttall//cms HA89 backcross) were dehulled using a single wheat-head thresher if possible or by hand. The seed was provided by the Pioneer sunflower research station at Woodland, Calif. Seeds were surface sterilized for 20 minutes in a 20% Chlorox bleach solution with the addition of two drops of Tween 20 per 50 ml of solution. The seeds were rinsed twice with sterile distilled water.

Disarmed *Agrobacterium tumefaciens* strain EHA 105 was used in all transformation experiments. Binary vector PHP10940 was introduced into EHA105 using a freeze-thaw transformation method (Holsters et al., Mol. Gen. Genet. 163: 181–187 (1978)). The plasmid contains plant expressed GUS and NPTII genes between the right and left T-DNA borders. In these experiments we used only the GUS gene to measure transformation response. Bacteria for plant transformation experiments were grown overnight (28° C. and 100 RPM continuous agitation) in liquid YEP medium (10 gm/l yeast extract, 10 gm/l Bactopeptone and 5 gm/l NaCl, pH 7.0) with 50 mg/l kanamycin. The suspension was used when it reached an $OD_{600}$ of about 0.5 to 1.5. The *Agrobacterium* cells were pelleted and re-suspended at a final $OD_{600}$ of 4.0 in an inoculation medium comprised of 12.5 mM MES pH 5.7, 1 gm/l $NH_4Cl$, and 0.3 gm/l $MgSO_4$.

The sunflower transformation protocol allows the recovery of transgenic progeny without the use of chemical selection pressure, therefore the NPTII gene in PHP10940 was not used. Dehulled and surface-sterilized seeds were imbibed in the dark at 26 C for 20 h on filter paper moistened with water. The cotyledons and root radical were removed, and the meristem explants were cultured on 374E (GBA medium consisting of MS salts, Shepard vitamins, 40 mg/l adenine sulfate, 3% sucrose, 0.5 mg/l 6-BAP, 0.25 mg/l IAA, 0.1 mg/l GA, and 0.8% Phytagar at pH 5.6) for 24 h in the dark. The primary leaves were removed to expose the apical meristem. Approximately 40 explants were placed with the apical dome facing upward in a 2 cm circle in the center of 374M (GBA medium with 1.2% Phytagar) and then cultured on the medium for 24 h in the dark. Particle bombardment of the explants with particles containing no DNA followed this culture step. The particle bombardment is done to provide improved conditions in the meristem tissue for Agrobacterium T-DNA transfer.

Particle bombardment was done by resuspending approximately 18.8 mg of 1.8 μm tungsten particles in 200 μl absolute ethanol. Particles were sonicated briefly to create a uniform suspension, then 10 μl of it was dropped on the center of the surface of macrocarrier. Each plate was bombarded twice using a BioRad PDS1000/He helium gun with 650 psi rupture discs. The plates are bombarded on the first shelf of the gun at 26 mm Hg vacuum.

Particle-bombarded explants were spread out on the 374M plates and a droplet of Agrobacterium suspension was placed directly onto the top of each meristem. The explants were co-cultivated on 374M medium for 4 days then transferred to 374 C medium (GBA with 1% sucrose and no BAP, IAA, or GA3 and supplemented with 250 μg/ml cefotaxime). The plantlets were cultured on 374C medium for about 2 weeks in a culture room set up for 18 h day and a constant temperature of 26 C.

Sunflower shoots developed in the two-week culture period following transformation. The shoots were then sacrificed to GUS staining in order to quantify the transformation response. The staining was used to identify transformed sectors on T0 shoots. The GUS staining protocol included McCabe's GUS staining solution. Transformation response was quantified by noting both the frequency of transformed sectors and the quality of the sectors.

Transformation Frequency of SMF3 Hybrids with Elite Sunflower Genetics

A number of hybrid sunflower lines were developed that involved crossing commercial line genetics with SMF3. Commercial lines of sunflower generally do not perform as well as SMF3 in tissue culture and are also difficult to transform. However, SMF3 is agronomically inferior to commercially available inbreds. This inferiority leads sunflower breeders to initiate numerous backcross cycles using commercially viable inbreds as recurrent parents in order to obtain commercially viable inbreds having the trait conferred by transformation, but lacking the inferior traits of SMF3. Experiments were conducted to determine if the transformation competence of SMF3 could be conferred to lines constituted by hybridizing SMF3 with commercial inbreds. SMF3 was identified as the transformation competence donor genotype, while commercial inbreds constitute the transformation recipient genotypes. The ability to successfully transform the described hybrids at high rates would permit breeders to reduce their use of backcrossing. This would occur since (1) the hybrid would possess 50% genetic contribution from the elite parent and (2) there would theoretically be a 50% probability that single transformation events occurred within the chromosomes donated by the elite parent. When transformation of the elite chromosome occurs, the tranformation event has a higher probability of being genetically linked with favorable traits and this in turn, reduces the need for backcrossing in order to derive a commercially viable inbred. These hybrids were developed using SMF3 as both a female (pollen recipient) and as a male (pollen donor).

*Agrobacterium* transformation in these experiments was done according to the standard protocols used for SMF3. The goal of each experiment was to do side by side comparisons of the transformation response of the hybrid and both of the parental lines, SMF3 and a commercial line. Two weeks after the inoculation with Agrobacterium, sunflower shoots were removed from tissue culture and placed in GUS stain. Individual cells and/or sectors of transformation on the shoots turn blue and were used to quantify the transformation response. If there are sectors that include tissues that give rise to germ line cells, then it is possible to recover the transgene in the next generation of seed. This is the most desirable result and the lack of this sector type contributes largely to the difficulty of commercial line transformation. Quantifying the transformation response included noting how many sectors have the potential to contribute to the germ line. GUS staining observed on transformed sunflower was divided roughly into 4 categories (Table 1). The categories include 1) small transformed cell patches and sectors which most likely do not have the potential to contribute to the germ line on the lower part of the shoots; 2) sectors of transformation that most likely would contribute to the germ line on the lower parts of the shoots; 3) long sectors that develop to the upper parts of the shoot that would not contribute to germ line transformation; and 4) larger sectors that develop to the upper parts of the shoot that are likely to contribute to germ line transformation. The sector types that most often result in transgenic seed are those described in phenotype 2 and 4 (Table 1).

The transformation response of PR126M alone or in combination with SMF3 is an example of the increased frequency that you can obtain with the hybrid combination (Table 2). This commercial line showed a relatively good transformation response compared to the other commercial lines that were tested. In the first experiment (Table 2), PR126M responded as well as the SMF3 X PR126M hybrid. The enhancement contributed by SMF3, however, was observed in experiments two and three. A more dramatic difference is observed using a line with a very poor transformation response such as VK89M (Table 4). VK89M showed a 10–15% transformation response. In contrast, the SMF3 X VK89M hybrid exhibited approximately a three-fold increase in transformability over VK89M. A similar result occurred when SMF3 was hybridized with PK68G. The transformation response of the hybrid SMF3 X PK68G was almost double that of PK68G per se (Table 3). In all of the experiments listed in Tables 2–4, SMF3 was used as the female in the pollinations.

We also tested the transformation response of lines where SMF3 was used as the pollen donor (male) in making commercial line hybrids (Table 5). Experiments conducted with some of these hybrid lines also showed improved transformation response. The best examples for improvement are shown by inbreds VK40 and RXT004L (Table 5). The hybrid combination VK40F X SMF3 showed a 3 fold increase over inbred line VK40G. A similar increase was also seen for RXT004LF X SMF3 over RXT004LG.

Of the fifteen combinations tested, in only one case was the transformation frequency of the SMF3 hybrid reduced relative to the commercial inbred transformation recipient (SMF3x VDK612LG) In contrast, twelve of the fifteen combinations tested showed moderate to dramatic increases in transformation frequency in the hybrid relative to the commercial inbred transformation recipient.

TABLE 20

DESCRIPTION OF CATEGORIES OF GUS PHENOTYPES SCORED IN HYBRID SUNFLOWER TRANSFORMATION EXPERIMENTS

| Phenotype | Description |
| --- | --- |
| Phenotype 1 | spots (cells) and streaks (cell files) at the base of the shoots |
| Phenotype 2 | sectors and developing secondary shoots with sectors at the base of the shoots |
| Phenotype 3 | spots (cells) and streaks (cell files) that develop all the way to the top of the shoots |
| Phenotype 4 | sectors that develop all the way to the top of the shoot (includes the broad leaf sectors at the tops of shoots) |

TABLE 21

TRANSFORMATION RESPONSE OF PR126M, SMF3, AND SMF3 HYBRIDS WITH PR126M

| Ex. | Line | Shoots (no.) | GUS Pos. (no.) | Phen 1 (no.) | Phen 2 (no.) | Phen 3 (no.) | Phen 4 (no.) | Phen 2 + 4 (no.) |
| --- | --- | --- | --- | --- | --- | --- | --- | --- |
| 1 | PR126M | 70 | 54 (77%) | 11 | 8 | 8 | 27 | 35 (50%) |
|  | SMF3 | 68 | 60 (88%) | 14 | 20 | 3 | 23 | 43 (63%) |
|  | SMF3 × PR126M | 70 | 65 (93%) | 17 | 15 | 13 | 20 | 35 (50%) |
| 2 | PR126M | 98 | 79 (81%) | 15 | 17 | 23 | 24 | 41 (42%) |
|  | SMF3 | 118 | 109 (92%) | 13 | 33 | 21 | 42 | 75 (64%) |
|  | SMF3 × PR126M | 82 | 78 (95%) | 17 | 12 | 22 | 27 | 39 (48%) |

TABLE 21-continued

TRANSFORMATION RESPONSE OF PR126M, SMF3, AND SMF3 HYBRIDS WITH PR126M

| Ex. | Line | Shoots (no.) | GUS Pos. (no.) | Phen 1 (no.) | Phen 2 (no.) | Phen 3 (no.) | Phen 4 (no.) | Phen 2 + 4 (no.) |
|---|---|---|---|---|---|---|---|---|
| 3 | PR126M | 65 | 55 (85%) | 23 | 6 | 16 | 10 | 16 (25%) |
|  | SMF3 | 76 | 73 (96%) | 14 | 24 | 9 | 26 | 50 (66%) |
|  | SMF3 × PR126M | 56 | 51 (91%) | 13 | 8 | 14 | 16 | 24 (43%) |

TABLE 22

TRANSFORMATION RESPONSE OF PK68G, SMF3, AND SMF3 HYBRIDS WITH PK68G

| Ex. | Line | Shoots (no.) | GUS Pos. (no.) | Phen 1 (no.) | Phen 2 (no.) | Phen 3 (no.) | Phen 4 (no.) | Phen 2 + 4 (no.) |
|---|---|---|---|---|---|---|---|---|
| 1 | PK68G | 73 | 52 (71%) | 19 | 9 | 11 | 13 | 22 (30%) |
|  | SMF3 | 39 | 34 (87%) | 6 | 16 | 2 | 10 | 26 (67%) |
|  | SMF3 × PK68G | 73 | 67 (92%) | 19 | 17 | 13 | 18 | 35 (48%) |
| 2 | PK68G | 60 | 53 (88%) | 23 | 11 | 12 | 7 | 18 (30%) |
|  | SMF3 | 43 | 37 (86%) | 8 | 12 | 4 | 13 | 25 (58%) |
|  | SMF3 × PK68G | 63 | 54 (86%) | 16 | 17 | 8 | 13 | 30 (48%) |

TABLE 23

TRANSFORMATION RESPONSE OF VK89M, SMF3, AND SMF3 HYBRIDS WITH VK89M

| Ex. | Line | Shoots (no.) | GUS Pos. (no.) | Phen 1 (no.) | Phen 2 (no.) | Phen 3 (no.) | Phen 4 (no.) | Phen 2 + 4 (no.) |
|---|---|---|---|---|---|---|---|---|
| 1 | VK89M | 84 | 33 (39%) | 9 | 4 | 11 | 9 | 13 (15%) |
|  | SMF3 | 87 | 76 (87%) | 15 | 21 | 7 | 33 | 54 (62%) |
|  | SMF3 × VK89M | 23 | 21 (91%) | 6 | 7 | 5 | 3 | 10 (43%) |
| 2 | VK89M | 86 | 60 (70%) | 33 | 5 | 16 | 6 | 11 (13%) |
|  | SMF3 | 53 | 48 (91%) | 8 | 17 | 6 | 17 | 34 (64%) |
|  | SMF3 × VK89M | 80 | 75 (94%) | 27 | 18 | 14 | 16 | 34 (43%) |

TABLE 24

TRANSFORMATION RESPONSE OF COMMERCIAL LINE INBREDS, SMF3, AND COMMERCIAL LINE HYBRIDS WITH SMF3

| Ex. | Line | Shoots (no.) | GUS Pos. (no.) | Phen 1 (no.) | Phen 2 (no.) | Phen 3 (no.) | Phen 4 (no.) | Phen 2 + 4 (no.) |
|---|---|---|---|---|---|---|---|---|
| 1 | VK106G | 24 | 14 (58%) | 11 | 1 | 0 | 2 | 3 (13%) |
|   | VK106F × SMF3 | 59 | 54 (92%) | 25 | 5 | 13 | 11 | 16 (27%) |
|   | VK40G | 50 | 35 (70%) | 15 | 5 | 11 | 4 | 9 (18%) |
|   | VK40F × SMF3 | 59 | 55 (93%) | 10 | 16 | 10 | 19 | 35 (59%) |
|   | SMF3 | 53 | 52 (98%) | 7 | 15 | 7 | 23 | 38 (72%) |
| 2 | SWK002LG | 9 | 1 (11%) | 0 | 1 | 0 | 0 | 1 (11%) |
|   | SWK002LF × SMF3 | 43 | 20 (47%) | 10 | 0 | 6 | 4 | 4 (9%) |
|   | RXT004LG | 34 | 25 (74%) | 16 | 0 | 6 | 3 | 3 (9%) |
|   | RXT004LF × SMF3 | 39 | 30 (77%) | 13 | 8 | 6 | 3 | 11 (28%) |
|   | VK820F | 18 | 11 (61%) | 5 | 0 | 3 | 3 | 3 (17%) |
|   | VK820F × SMF3 | 44 | 42 (95%) | 17 | 7 | 13 | 5 | 12 (27%) |
|   | SMF3 | 43 | 42 (98%) | 14 | 12 | 7 | 9 | 21 (49%) |
| 3 | LC1019G | 25 | 23 (92%) | 11 | 5 | 4 | 3 | 8 (32%) |
|   | LC1019F × SMF3 | 47 | 42 (89%) | 18 | 6 | 7 | 11 | 17 (36%) |
|   | D99G | 35 | 22 (63%) | 6 | 5 | 6 | 5 | 10 (21%) |
|   | D99F × SMF3 | 53 | 41 (77%) | 17 | 2 | 13 | 9 | 11 (29%) |
|   | VKD612LG | 54 | 50 (93%) | 9 | 16 | 6 | 19 | 35 (65%) |
|   | VKD612LF × SMF3 | 45 | 30 (67%) | 15 | 6 | 5 | 4 | 10 (22%) |
|   | SMF3 | 102 | 99 (97%) | 27 | 25 | 14 | 33 | 58 (57%) |

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A method of developing a maize embryo that has increased transformation efficiency comprising crossing a Hi-II maize plant to a different maize plant other than a second Hi-II maize plant, to obtain a maize embryo; wherein said embryo has increased transformation efficiency when compared to a transformation efficiency of an embryo from said different maize plant and; wherein said transformation efficiency of the embryo and the transformation efficiency of the embryo of said different maize plant are measured using the same experimental conditions.

2. The method of claim 1 wherein the Hi-II plant is a male parent.

3. The method of claim I wherein the Hi-II plant is a female parent.

* * * * *